(12) United States Patent
Shi et al.

(10) Patent No.: US 10,479,976 B2
(45) Date of Patent: Nov. 19, 2019

(54) BUOYANCY ENABLED SEPARATION METHOD AND SYSTEM

(71) Applicant: DIAGNOLOGIX, LLC, San Diego, CA (US)

(72) Inventors: Guixin Shi, San Diego, CA (US); Kimberly Liu, San Diego, CA (US); Ying-Ting Wang, San Diego, CA (US)

(73) Assignee: Diagnologix, LLC, San Diego, CA (US)

( * ) Notice: Subject to any disclaimer, the term of this patent is extended or adjusted under 35 U.S.C. 154(b) by 35 days.

(21) Appl. No.: 15/842,803

(22) Filed: Dec. 14, 2017

(65) Prior Publication Data

US 2018/0171295 A1 Jun. 21, 2018

Related U.S. Application Data

(60) Provisional application No. 62/435,083, filed on Dec. 16, 2016.

(51) Int. Cl.
*G01N 33/536* (2006.01)
*C12N 5/0783* (2010.01)
(Continued)

(52) U.S. Cl.
CPC ........... *C12N 5/0636* (2013.01); *C12M 47/02* (2013.01); *C12N 5/0087* (2013.01); *C12N 5/0093* (2013.01); *G01N 33/536* (2013.01); *G01N 33/538* (2013.01); *G01N 33/544* (2013.01); *G01N 33/5432* (2013.01);
(Continued)

(58) Field of Classification Search
None
See application file for complete search history.

(56) References Cited

U.S. PATENT DOCUMENTS 6,264,917 B1 7/2001 Klaveness et al.
6,352,694 B1 3/2002 June et al.
(Continued)

FOREIGN PATENT DOCUMENTS

WO 2013011011 1/2013
WO 2015175344 11/2015

OTHER PUBLICATIONS

Thermofisher Scientific: Dynabeads Human T-Activator CD3/CD28—For Physiological Activation of Human T Cells; https://www.thermofisher.com/us/en/home/references/protocols/proteins-expression-isolation-and-analysis/t-cell-activation-and-expansion/dynabeads-human-t-activator-cd3-cd28.html.
(Continued)

*Primary Examiner* — Christopher L Chin
(74) *Attorney, Agent, or Firm* — Schlee IP International, P.C.; Alexander R. Schlee

(57) ABSTRACT

A buoyancy enabled separation method for isolation from a sample including a variety of different cells a sparse subset of cells that is differentiated by a plurality of different cell surface markers. Microbubbles conjugated to antibodies are applied sequentially in a container with the previously used microbubbles disrupted prior to applying the next microbubbles conjugated to a different antibody. A system that includes a syringe-like container with a plunger and closeable opening. Further, a method for activating and expanding isolated T cells by applying antigen presenting microbubbbles having a flexible lipid shell mimicking an antigen presenting cell for generating immunological synapses.

16 Claims, 17 Drawing Sheets

(51) Int. Cl.
*G01N 33/538* (2006.01)
*G01N 33/543* (2006.01)
*G01N 33/544* (2006.01)
*C12N 5/00* (2006.01)
*C12M 1/00* (2006.01)

(52) U.S. Cl.
CPC .... *C12N 2501/50* (2013.01); *C12N 2501/515* (2013.01); *C12N 2501/599* (2013.01)

(56) References Cited

U.S. PATENT DOCUMENTS

| | | | |
|---|---|---|---|
| 2003/0104359 A1* | 6/2003 | Cuthbertson | A61K 49/223 435/5 |
| 2009/0176201 A1* | 7/2009 | Jablonski | G01N 33/54313 435/5 |
| 2015/0219636 A1* | 8/2015 | Rychak | G01N 33/5432 435/5 |
| 2017/0037369 A1 | 2/2017 | Ramsborg et al. | |

OTHER PUBLICATIONS

Stemberger, Christian, et al.: Novel Serial Positive Enrichment Technology Enables Clinical Multipartner Cell Snorting; PLOS ; Apr. 24, 2012; http://journals.plos.org/plosone/article?id=10.1371/journal.pone.0035798.

Shi, X., 'Buoyancy-based separation of antigen-specific T cells', Thesis, University of California, San Diego, Jan. 1, 2016, pp. 1-76. See pp. 32, 33, 37, 56-58, 63-65 and 69.

Turtle, C. J. et al., 'Artificial antigen-presenting cells for use in adoptive immunotherapy', Cancer Journal, 2010, vol. 16, No. 4, pp. 374-381, NIH Public Access Author Manuscript Version (internal pp. 1-16) See abstract; p. 2, 4th paragraph; pp. 4, 5 and 7; figures 1 and 3.

Shi, G. et. al., 'Isolation of rare tumor cells from blood cells with buoyant immuno-microbubbles', PloS One, Mar. 13, 2013, vol. 8, No. 3, e58017 (internal pp. 1-9) See the whole document.

International Search Report of parallel PCT/US2017/066525.

* cited by examiner

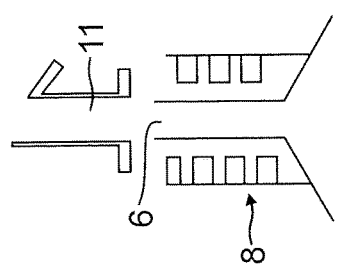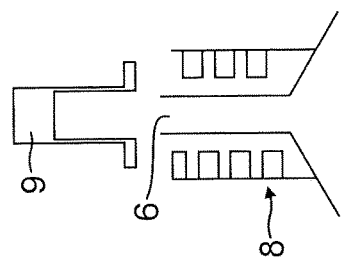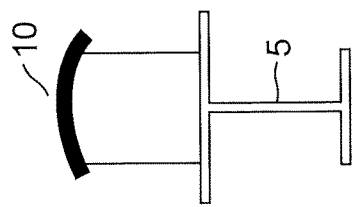

FIG. 18
(a)
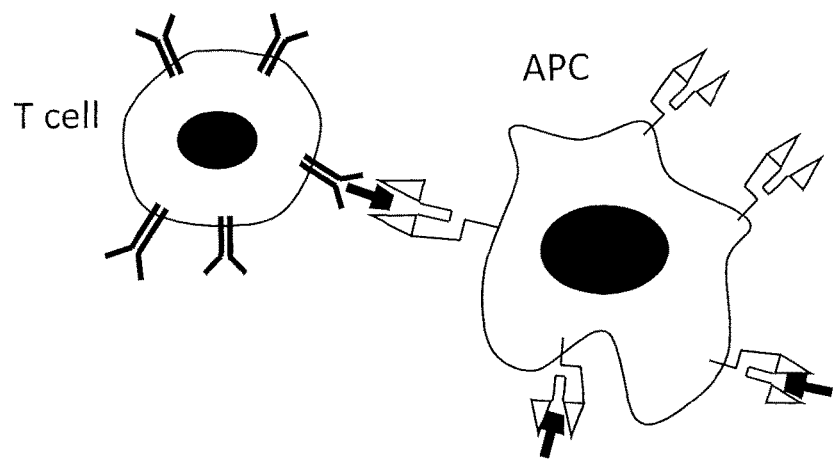
(b)
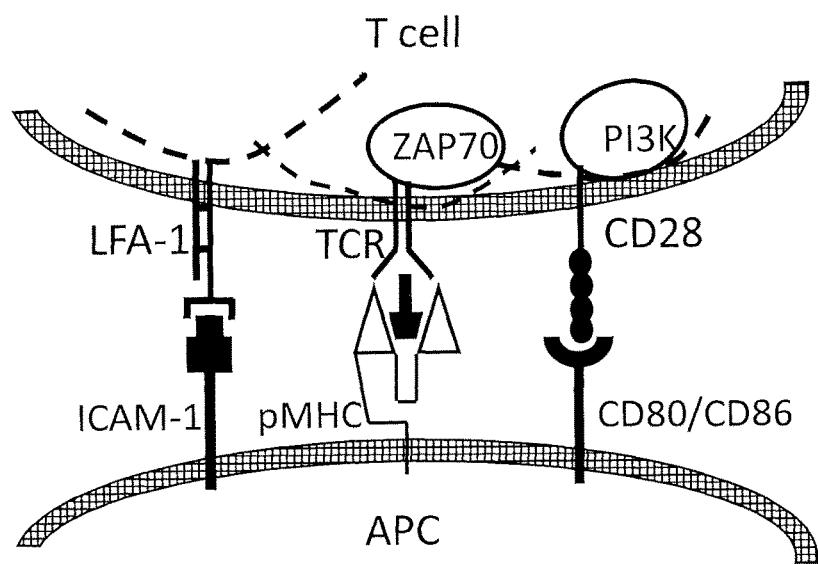

FIG. 20
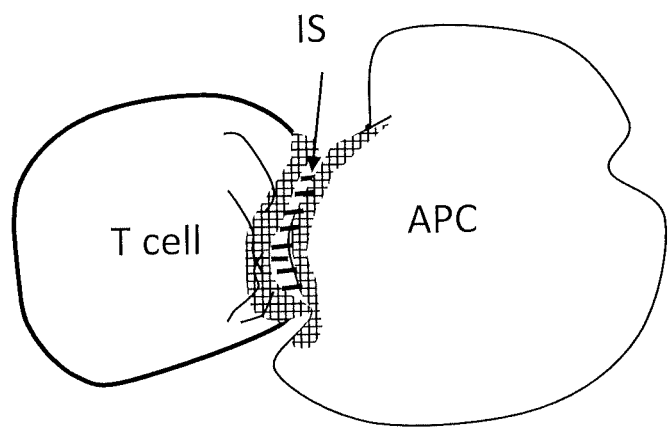
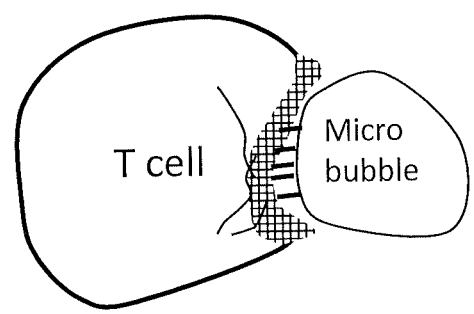

FIG. 23

|  | MACS | Streptamers | Microbubbles |
|---|---|---|---|
| Starting | PBMC | PBMC | PBMC |
| Selection | Paramegnetic beads-CD3 to collect all T cells <br><br> Wash | Streptamer-CD8 to collect T cells <br> ↓ wash <br> Biotin → Strep-CD62L <br> ↓ wash <br> Biotin → Strep-CD45RA <br> ↓ wash <br> Biotin | In one BUBLES-device incubate with CD8- MB, then invert and discard waste, apply pressure, then repeat for CD62L and CD45RA |
| Culture | Transfer cells to culture bag +media +cytokines +stimulators | Transfer cells to culture bag +media +cytokines +stimulators | In the same device +media +cytokines +stimulators |
| CAR eng | Transfer to vector loaded bag for gene transduction | Transfer to vector loaded bag for gene transduction | In the same device, inject vectors for gene transduction |
| Expansion | Transfer to new culture bag to expand CAR-T cells | Transfer to new culture bag to expand CAR-T cells | Culture in same device or optional transfer to a culture bag to expand CAR-T cells |
| Beads removal | Apply magnetic power to remove beads from cells | Not required, performed in selection cycles | Not required |
| Final products | Wash, resuspend Transfer to infusion | Wash, resuspend Transfer to infusion | BUBLES device to concentrate for infusion |

BUOYANCY ENABLED SEPARATION METHOD AND SYSTEM

CROSS-REFERENCE TO RELATED APPLICATION

This application claims priority to U.S. provisional application 62/435,083 filed on Dec. 16, 2016 herein Incorporated in its entirety by reference.

STATEMENT REGARDING FEDERALLY SPONSORED RESEARCH

This invention was made with government support under 1R43CA176892-01A1, 3R43CA176892-01A1S1, 2R44CA176892, 1R43HL126285-01, 2R44HL126285-02A1, and HHSN261201700051C awarded by the National Institutes of Health. The government has certain rights in the invention.

FIELD OF THE INVENTION

The present disclosure relates to a simple end-to-end device and system for the bulk isolation, serial multiple-marker sorting, stimulation, manipulation, culture, and expansion of cells and other biological agents.

BACKGROUND OF THE INVENTION

A major challenge for all cell therapies is the need to develop cost-effective and efficient manufacturing and delivery capabilities, such as creating a scalable, automated closed system to isolate a subset of T cells. For example, studies in mice and humans show that the infusion of less differentiated T cells that are genetically engineered with chimeric antigen receptor (CAR) or T cell receptor (TCR) leads to superior cell expansion, persistence, and cancer elimination. Sorting and isolating a subset of T cells (e.g. naïve CD8+ cells) requires multiple markers (e.g. CD8, CD62L & CD45RA), which is challenging to scale up and automate.

FACS (fluorescence activated cell sorting) is the product most used for the detailed analysis of individual cells. Using FACS, it is difficult to scale up for bulk isolation of cells. Magnetic cell sorting (MACS) techniques, particularly the Miltenyi system, are used for targeted cell isolation in bulk. Cells bound to microbeads (e.g. Dynabeads) can be pulled out by an external magnet outside the mixing tube. However, binding antibody-conjugated microbeads to cells, rather than antibodies alone or antibody-conjugated nanobeads, slows down the process. Therefore, most magnetic cell sorting systems on the market use nanobead over microbead-conjugated antibodies. One of the biggest problems with MACS is that isolated cells coupled to magnetic microparticles (>1 μm) are often destroyed.

Existing MACS technology applies high-gradient magnetic cell separation columns to magnetize nanobead-labeled cells in a magnetic field, generated by a strong external magnet. MACS uses ferromagnetic steel-wool filled columns to strengthen the long-distance interaction between the low magnetic nanobeads and the external magnet. However, the use of the steel-wool packed column in this system creates other technical problems like column clogging and increased manufacturing costs. Moreover, the MACS nanobeads stick to the targeted cells, either on the cell surface or inside by endocytosis. This limits the application of MACS primarily to cell enrichment based on a single surface marker.

As described in the International Patent Application published under the publication number WO 2015/175344 A1, a BUBLES (buoyancy enabled separation) or buoyancy activated cell sorting (BAGS) technology by applying targeted microbubbles for cell isolation has been developed for cell isolation.

For multi-parameter MACS, the prior art contains a few methods enabling the reversible binding of cells and affinity ligand-conjugated magnetic beads. These were developed by sequentially targeting multiple cell-surface markers. For example, the Streptamer technology enables the reversible target cell binding of magnetic microparticles (~1 μm) by conjugating to Strep-Tactin multimerized low-affinity single-chain antibodies that have been engineered to fuse with a Strep-tag. Other technologies in the prior art use modified antibodies that can dissociate from cells or magnetic beads. These methods usually require extensive modifications to the antibodies of interest and can be applied to other platforms beyond MACS, such as FACS, BAGS and other forms of affinity purification.

WO 2015/175344 A1 teaches a BACS method for clinical applications, including the isolation of circulating tumor cells and cord blood stem cells. This technology has several advantages over other prior art in performing bulk cell isolation. First, its lipid shell microbubble is self-molding to external forces (e.g. ultrasound and bound cells) because it is the most compressible and flexible shell-class microbubbles (others including albumin, polymer, and glass). In conjunction with a gas core, it is a very gentle material for cell isolation. Second, the microbubble it uses is a "self-driving vehicle", as microbubble-bound cells automatically float to the top surface of a liquid. Third, the lipid-shelled microbubbles it uses self-separate from water-based solutions and self-concentrate/aggregate to other microbubbles. Fourth, users of this technology working with cell-bound microbubbles can disrupt their internal bonds, without causing cell damage, by increasing ambient air pressure.

Emulsification is used to prepare perflorohexane gas microbubbles (MBs) within phospholipid shells. DSPE-PEG 3400-maleimide is used in the microbubble membrane to conjugate antibodies to the microbubbles. It uses Fc fragment-specific IgG carrying 1-2 thiol groups per antibody to conjugate antibodies onto maleimide-activated MBs via Michael addition. The technology uses targeting antibodies, such as anti-EpCAM, the most widely accepted marker for isolating circulating tumor cells of epithelial origin for coupling. Most the MBs in this process have a diameter of 3-10 μm. Each MB has, on average, 367,000 anti-Fc IgG molecules.

BAGS (or BUBLES) is an innovative cell isolation/sorting platform that can be used alone or in combination with the other two major platforms in the prior art (FACS and MACS) for challenging tasks. In its preferred embodiment, the present disclosure uses BACS for the bulk isolation, multiple-marker sorting, and manipulation of human cells in a single container device. In other embodiments, the present disclosure uses BACS in conjunction with FACS or MACS for this isolation, sorting, and manipulation process.

Cell based therapy is a rapidly developing medicine of intense research and great potential to patient benefits. The majority of cell therapies in clinical trials today are hematopoietic or mesenchymal stem cells and immune T cells for genetic diseases and cancers, these targeted cells have common and well known characteristics of being very rare subsets and the need of multiple cell surface markers for specific isolation from the heterogeneous cell mixtures in blood or human tissues, and of being very difficult to regulate cell differentiation progress or maintain cell stemness during isolation, expansion and in vitro manipulation procedures. This invention is intended to overcome a number of these obstacles.

SUMMARY OF THE INVENTION

Apart from many other objects of the invention, it is an object to overcome two major challenges for all cell therapies, namely (1) a robust manufacturing procedure to cost-effectively scale up the sufficient quantity of targeted cells; and (2) the capability to control and maintain the biological characteristics of targeted cells prior to clinical administration to patients. It is another object of the invention to accomplish the aforementioned goals (1) and (2) by a simple end-to-end device and system providing technology to overcome/improve these two challenges, more specifically to provide the bulk isolation, serial multiple-marker sorting, stimulation, manipulation, culture, and expansion of cells and other biological agents in a sterile environment that is safe from contamination for the sequential steps of accomplishing the aforementioned goals.

According to a first aspect of the invention, a buoyancy enabled separation method is created for isolation from a sample including a variety of different cells a sparse subset of cells that is differentiated by a plurality of different cell surface markers, comprising: a) placing the sample in a container; b) adding first flexible shell microbubbles having a flexible shell with an inner bubble wall enclosing a gas and an outer bubble wall conjugated to a first antibody capable of binding to a first cell surface marker of a first subset of cells encompassed in the liquid sample; c) incubating over a time span sufficient to allow an interaction between the first antibody and the first cell surface marker binding the first antibody to the first cell surface marker; d) allowing the first microbubbles with the first subset of cells bound to the first microbubbles to separate by flotation from a remainder of the sample; e) removing waste from the container, including cells within the sample other than the first subset of cells; f) disrupting the first microbubbles such that the first set of isolated cells are no longer buoyant; g) adding second flexible shell microbubbles having a flexible shell with an inner bubble wall enclosing a gas and an outer bubble wall conjugated to a second antibody capable of binding to a second cell surface marker of a second subset of cells encompassed within the first subset of cells; h) incubating over a time span sufficient to allow an interaction between the second antibody and the second cell surface marker binding the second antibody to the at least one second cell surface marker; i) allowing the microbubbles with the second subset of cells bound to the microbubbles to separate by flotation from a remainder of the sample; and j) removing waste from the container, including cells within the first subset of cells other than the second subset of cells.

According to a second aspect of the invention, a system for performing the aforementioned method is created, comprising: a container having an inner wall defining an inner container space; a plunger in sealing connection with the inner wall and a movable in relation to the inner wall; a port with an openable and closeable valve connecting the inner space to the environment for allowing gas, liquid and solid material to be fed into the inner space and out of the inner space; and flexible shell microbubbles within the inner container space, said microbubbles having a flexible shell with an inner bubble wall enclosing a gas and an outer bubble wall conjugated to a first antibody capable of binding to a first cell surface marker of a first subset of cells encompassed in the liquid sample.

According to a third aspect of the invention, a method for activating and expanding isolated T cells is created, comprising: a) adding to isolated T cells ligands presenting microbubbles having a flexible lipid shell with an inner bubble wall enclosing a gas and an outer bubble wall conjugated to ligands capable of achieving cell contact dependent juxtacrine signaling on the isolated T cells; and b) adding to isolated T cells ligands presenting microbubbles having a flexible lipid shell with an inner bubble wall enclosing a gas and an outer bubble wall conjugated to an antigen capable of forming an immunological synapse with the T cells.

DETAILED DESCRIPTION OF THE INVENTION

An embodiment of the invention is referred to the Buoyancy enabled separation method and system for clinical applications, in the following referred to by the acronym BUBLES, including the isolation of circulating tumor cells, cord blood stem cells and T lymphocytes. This technology has several advantages over others in performing bulk cell isolation. First, its lipid shell microbubble is self-molding to external forces (e.g. ultrasound and bound cells), because it is the most compressible and flexible shell of microbubbles, for instance compared to albumin, polymer or glass. In conjunction with a gas core, it is a very gentle material for cell isolation. Second, the microbubble is a "self-driving vehicle", as microbubble-bound cells automatically float to the top surface of a liquid. Third, the lipid-shelled microbubbles self-separate from water-based solutions and self-concentrate/aggregate to other microbubbles. Fourth, cell-bound microbubbles can be disrupted from their internal bonds, without causing cell damage, by increasing ambient air pressure. The following sections will describe how these unique advantages of microbubble can help resolve the cell therapy challenges.

BRIEF DESCRIPTION OF THE DRAWINGS

The embodiments are illustrated by way of example and not limitation in the figures of the accompanying drawings in which like references indicate like elements.

FIG. 5 schematically shows a connecting/closing mechanism comprised in the system in accordance with an embodiment of the invention.

FIG. 6 schematically shows another connecting/closing mechanism comprised in the system in accordance with an embodiment of the invention.

FIG. 7 schematically shows a plunger comprised in the system in accordance with an embodiment of the invention.

FIG. 8 schematically shows another plunger comprised in the system in accordance with an embodiment of the invention.

FIG. 18 schematically demonstrates the interaction of ligands and receptors between the T cells and antigen presenting cells (APCs).

FIG. 20 schematically shows an immunological synapse between a T cell and APC, and according to an embodiment of the invention, an immunological synapse between a T cell and a microbubble simulating APC.

FIG. 23 shows a chart summarizing a comparison between the three methods MACS, Streptamers and Microbubbles.

DETAILED DESCRIPTION OF THE DRAWINGS

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment, and such references mean at least one.

The use of headings herein is merely provided for ease of reference and shall not be interpreted in any way to limit this disclosure or the following claims.

Reference in this specification to "one embodiment" or "an embodiment" or the like means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not other embodiments.

The present disclosure is comprised of a device and system for the bulk isolation, sorting, stimulation, expansion, and manipulation of cells and other biological agents in a single container. In its preferred embodiment, the present disclosure uses serial BACS (or BUBLES), with antibody-based affinity ligands attached to microbubbles, to repeatedly isolate, sort, stimulate, expand or manipulate human cells in a single, closed container.

Figure 1:
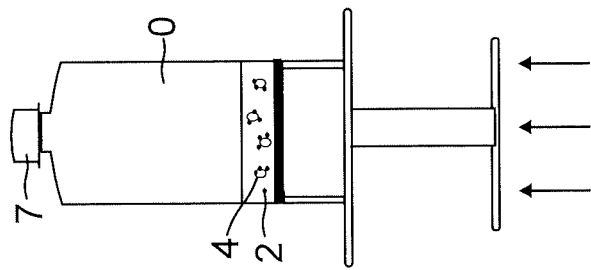
FIG. 1 shows the system according to an embodiment of the invention in a first configuration.
Figure 2:
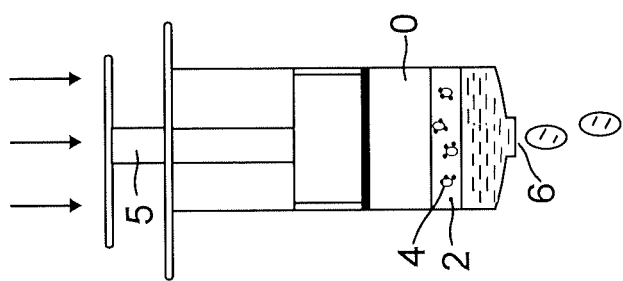
FIG. 2 shows the system according to an embodiment of the invention in a second configuration.
Figure 3:
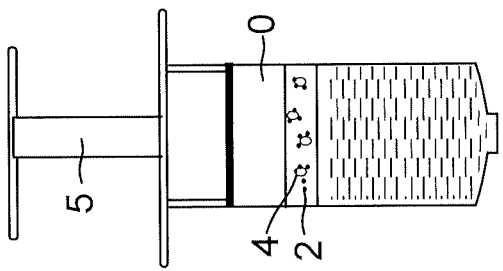
FIG. 3 shows the system according to an embodiment of the invention in a third configuration.
Figure 4:
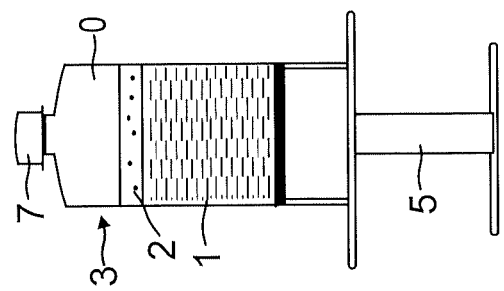
FIG. 4 shows the system according to an embodiment of the invention in a fourth configuration.

FIGS. 1-4 demonstrate one variation of the present disclosure's preferred embodiment. Here, the sample cells 1 are peripheral blood mononuclear cells (PBMC) 1 are mixed and incubated with anti-CD8 microbubble 2 in a syringe-like container 3. Microbubbles 2 and targeted cells 4 gradually float to the liquid surface (FIG. 2). The targeted cell 4 population (CD8+ cells) is retained (positive selection) by pushing the plunger 5 (FIG. 3) with the container opening 6 facing the ground (FIG. 2). For this positive selection, the majority of liquid is discarded. The microbubbles 2 are subsequently disrupted by increasing ambient air pressure in the air space 0 within the container, which is created by compressing air when a cap 7 is installed to the opening of the container (FIG. 4), for instance by moving the plunger. For the next cycle of BACS, the second type of targeted microbubble 2 (anti-CD62L) with buffer is mixed with the anti-CD8 sorted cells. The process restarts as previously described (FIGS. 2-4). After the $3^{rd}$ cycle with anti-CD45RA microbubbles 2, the naïve CD8+ T cell population (CD8+CD62L+CD45RA+) in the syringe-like container 3 is stimulated and expanded by binding to anti-CD3/anti-CD28 conjugated microbubbles 2 in culture medium. Subsequent manipulations (e.g. viral transduction with chimeric antigen receptors) can also be performed in the same container 3.

In the abovementioned figures, three consecutive positive selections are applied. Other applications may introduce steps for negative selection to remove targeted cells bound to microbubbles 2. Negative selection is achieved by adopting the orientation shown in FIG. 1 with the container opening 6 facing opposite to the ground instead of that showing in FIG. 2. In connection with an alternative device or adapter specifically suited for negative selection as it has been described in the international patent application publication WO 2015/175344 A1 and FIG. 6.

A preferred embodiment of the connecting/closing mechanism in the system of the invention comprises a standard Luer-Lok 8 that interfaces with a number of medical and laboratory instruments. An adaptor 9 or 11 seals the opening 6 at one end of the syringe-like container 3 to manipulate its affinity ligands conjugated microbubble, and cell contents and to collect harvested cells, and a plunger 5, with a plunger tip 10 modified to be convex or concave in shape, which fills the space between the affinity ligands conjugated microbubbles 2, and cells in solution, is inserted into the other end of the syringe-like container 3. The plunger may be operated automatically or manually. The shape of the plunger tip 10 may be adjusted or tuned by the mechanism for a diaphragm valve, as schematically shown by the arrows between FIGS. 7 and 8 demonstrating a back and forth the changing of the shape of the front face of the plunger 5. The shape of the plunger can be adjusted during use of the system to accommodate the needs of the user during different steps of the selection process. For instance, the plunger can be adjusted concave to accommodate more floated microbubbles and covex to expel more waste from the final product. These plunger front face shapes be also adjusted during the process to enhance the performance of each step. It is also possible to exchange plungers entirely for different steps, meaning that a kit is provided having a selection of plungers. Although this provides a simplification of the design, exchanging plungers between steps may not be preferred from a sterility point of view since it would involve opening the container other than through the cap 7, Luer Lok 8 or adaptor 9.

Other embodiments of the disclosure's device may consist of different hard or soft closed containers, different syringe-like container 3 configuration types, different adapter or plug types, different affinity ligand combinations, and plungers that are inverted at different angles or not inverted at all. The other embodiments may also isolate, sort, manipulate, stimulate, and expand other types of cells and biological agents. Finally, the other embodiments of the disclosure may use MACS or FACS in conjunction with BACS.

FIGS. 1-4 demonstrate one variation of the preferred embodiment of the present disclosure. In these figures, the closed container 3 consists of a simple syringe-like configuration with a plunger that may be closed with a cap as described above. Within the container 3 is an affinity ligands conjugated microbubble 2 solution that is used to isolate, sort, manipulate, stimulate, or expand sample cells or biological agents. The use of serial BACS (or BUBLES) for multi-marker sorting within a single container 3 is as described above.

To demonstrate serial multi-marker isolation of naïve T cells with targeted microbubbles, PBMC at $10^8$/ml in 0.2% BSA buffer were first incubated with anti-CD8 MB (microbubbles) in a syringe. The mixture in the syringe was gently rotated at 4° C. for 20 min. Subsequently, the syringe was kept in the position as shown in FIG. 2 for 10 min, followed by gently pushing the plunger to remove undesirable cells in solution, and to keep the buoyant MB layer as shown in FIG. 3. The retained MB layer was washed once by refilling 0.2% BSA buffer. Finally, the syringe was kept as shown in FIG. 4 and its opening of the syringe was sealed by a cap. The microbubbles were disrupted by pushing the plunger to increase ambient pressure to about 2-3 atm. The same procedure was repeated by applying anti-CD62L MB, followed by anti-CD45RA MB. FACS analyses demonstrated that the cell purity of each single-marker isolation was more than 80% for either one of the CD8+, CD62L+ or CD45RA+ populations. In the proof-of-concept serial multi-marker isolations, the CD8+/CD62L+/CD45RA+ triple positive cell population was enriched from 2% (original PBMC) to around 60 (40-80)%.

FIG. 5 demonstrates the top of a device from one of the present disclosure's preferred embodiments. Here, the syringe-like configuration comprising, in part, a closed container, uses a Luer Lok 8, allowing the device to interface with a variety of medical and laboratory instruments.

FIG. 6 demonstrates a cylindrical adaptor 9 is connected to the opening 6 of the syringe-like container 3, to seal the container for creating higher ambient pressure by pushing the plunger as demonstrated in FIG. 4 to disrupt microbubbles.

FIG. 6 demonstrates the top half of a device from another one of the present disclosure's preferred embodiments. Here, a different, inverted adaptor 11 is used to collect isolated, sorted, manipulated, expanded or stimulated cell sample. Otherwise, FIG. 6 is identical to FIG. 5.

Other types of adaptors, such as generic 2-way, 3-way or 4-way Luer Lok connectors, are connected to the opening 6 of the syringe-like container 3, for collecting sorted, isolated, manipulated, stimulated, or expanded sample in bulk following the repeated application of BACS in the closed container. Here, the sample is infused with an affinity ligands conjugated microbubble solution, and consists of target cells population from human blood and other body fluids or tissues.

FIG. 7 demonstrates the plunger 5 of a preferred embodiment. In this preferred embodiment, the plunger tip 10 of the plunger 5, which may be inter-converted to form a concave shape through a mechanism that controls a diaphragm valve or other similar devices. The tip is modified through the application of liquid or air pressure into the plunger 5. The configuration of the plunger tip 5 is used to manipulate targeted microbubbles 2 and infused human cells.

FIG. 8 demonstrates the plunger 5 according to another preferred embodiment. Here, the plunger tip 10 of the plunger, which may be inter-converted to form a convex shape through a mechanism that controls a diaphragm valve or other similar devices. Otherwise, FIG. 8 is identical to FIG. 7.

FIGS. 5-8 demonstrate the system used in one of the present disclosure's preferred embodiment. This system applies BACS and uses affinity ligands conjugated microbubbles 2 for the bulk isolation, sorting, manipulation, expansion, or stimulation of cells and other biological agents repeatedly in a closed container 3. In operating the system used in this particular preferred embodiment, a user would begin with the steps demonstrated in FIG. 1 or FIG. 2, then would follow the step demonstrated in FIG. 3, and finally would follow the step demonstrated in FIG. 4. After the step demonstrated in FIG. 4 is complete, the user could begin the process again, with another type of targeted microbubble 2, by returning to the steps demonstrated in FIGS. 2-4. These steps are performed repetitively to achieve bulk isolation, sorting, manipulation, stimulation, or expansion of the sample biological agent.

FIGS. 1-4 demonstrate a preferred embodiment of the present disclosure's BACS system, using microbubbles infused with targeted microbubbles. In the preferred embodiment of the device, the BACS system is applied in a syringe-like configuration comprising the closed container that uses a Luer Lok, an adapter rather than a plug, and a plunger with an inverted tip.

Figure 9:
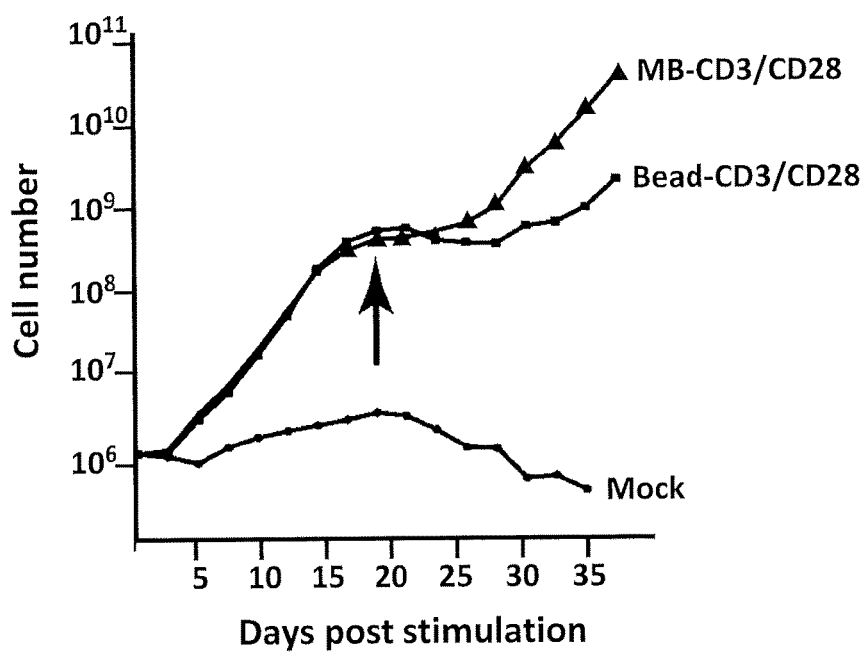
FIG. 9 demonstrates the cell proliferation results of a preferred embodiment of the invention involving the microbubbles in comparison to the prior art.
Figure 10:
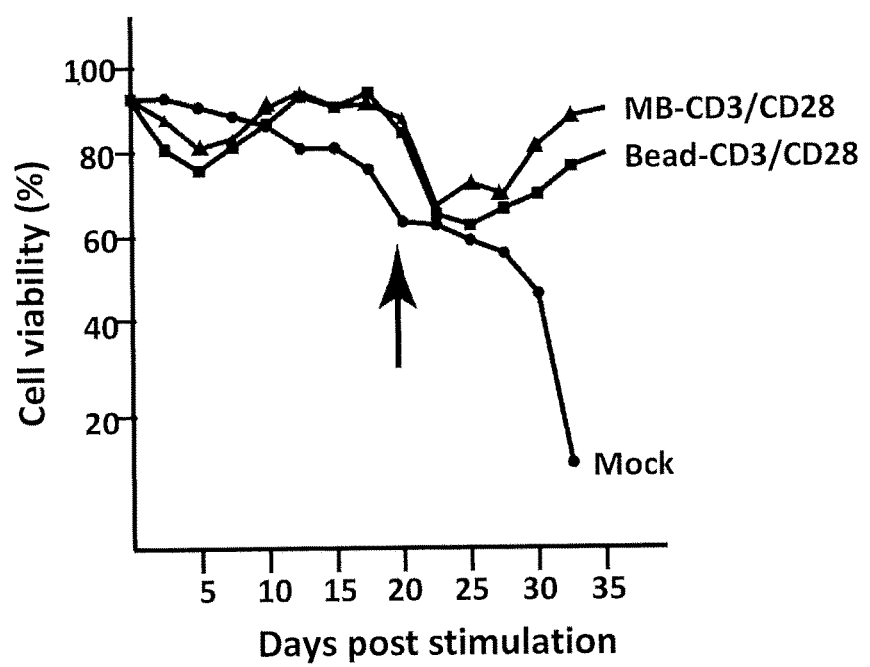
FIG. 10 demonstrates the cell viability results of a preferred embodiment of the invention involving the microbubbles in comparison to the prior art.

FIGS. 9-10 demonstrate the cell viability and proliferation results of a preferred embodiment of the present disclosure's microbubble solution relative to other embodiments of the present disclosure's solution and microbubble solutions existing in the prior art. In this preferred embodiment of the present disclosure's microbubble solution, CD3/CD28 affinity ligand combination conjugated microbubbles are infused for the isolation, sorting, expansion, manipulation, or stimulation of T cells. Both microbubble conjugated CD3/CD28 and Dynabead conjugated CD3/CD28 were added to the cell culture at the beginning and the time point where the arrow indicates on the graph. FIGS. 9-10 demonstrate this preferred embodiment achieving greater cell viability percentages and cell proliferation than solutions used in other embodiments of the present disclosure and in the prior art (Dynabeads). This superior outcome may reflect the more natural interaction between microbubbles and T cells to recapitulate immunological synapse.

Figure 11:
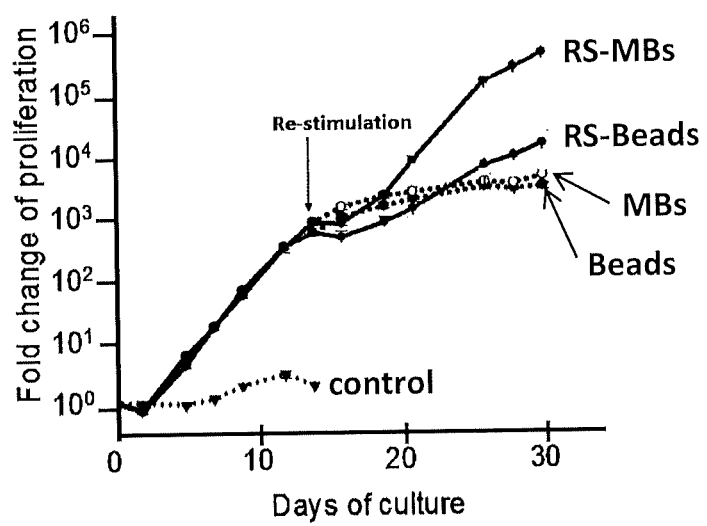
FIG. 11 demonstrates the fold changes of cell proliferation results of a preferred embodiment of the invention involving the microbubbles in comparison to the prior art.

FIG. 11 demonstrates a preferred embodiment of the present disclosure's microbubble solution. In FIG. 11, the microbubble solution is infused with microbubbles conjugated with CD3/CD28 ligand combination, after cell isolation in a single container has occurred. This anti-CD3/CD28 microbubble solution can be applied to expand T-cells with greater efficiency and quality than anti-CD3/CD28 Dynabeads, which were developed in the prior art. In Table 1, the cell expansion profile (CD8/CD4 T cell ratio) is preferred for use in cancer immunotherapy after CD3/CD28 stimulation.

Comparing the results between PBMC alone (PBMC group), PBMC+ anti-CD3/CD28 Dynabeads (Beads group) and PBMC+ anti-CD3/CD28 microbubbles (MB group), specifically comparing the performance of Beads and MB in case of multiple stimulation times, it becomes apparent that MB significantly outperform PBMC and Beads, specifically for higher orders of re-stimulation like second re-stimulation, as summarized in the following Table 1:

| Stimulation times | Groups | Culture Days | CD4 | CD8 | CD4/CD8 |
|---|---|---|---|---|---|
| 0 | PBMC | 0 | 48.3% | 10.2% | 60.5% |
| 0 | PBMC | 14 | 55.3% | 3.3% | 60.2% |
| 1x | Beads | 14 | 59.2% | 39.7% | 93.1% |
| 1x | MBs | 14 | 56.5% | 45.3% | 94.5% |
| 1x | Beads | 30 | 21.2% | 61.1% | 83.0% |
| 1x | MBs | 30 | 20.3% | 65.9% | 84.5% |
| 2x | Beads | 30 | 68.3% | 22.1% | 86.2% |
| 2x | MBs | 30 | 15.2% | 85.2% | 95.6% |

In other embodiments of the present disclosure, microbubbles can be conjugated with other types of ligands for similar cell-contact dependent signaling applications.

In the embodiments of the present disclosure, whether preferred or not, and whether demonstrated or not, affinity ligand combinations infused microbubbles can be disrupted over time or more precisely controlled by applying higher ambient pressure, which enables the creation of a convenient feeder-cell free cell contact dependent cell culture system.

Practical Application of the BUBLES Technology for Providing a Robust Manufacturing Procedure For the BUBLES (or BAGS) technology emulsification methods to prepare perflorohexane gas microbubbles (MBs) with a phospholipid shell, as for instance described in the international patent application publication WO 2015/175344 A1, DSPE-PEG 3400-maleimide was included in the membrane in order to conjugate the antibody Fc fragment-specific IgG carrying 1-2 thiol groups per antibody was conjugated onto maleimide-activated MBs via Michael addition. Targeting antibodies, such as anti-EpCAM, were coupled in the second step. The majority of the MBs had a diameter of 3-10 µm (similar to the size of most mammalian cells). Each MB had, on average, 367,000 anti-Fc IgG molecules. Recently, we and others used the same approach to successfully manufacture microbubbles that target other cell surface proteins, including Her2, EGFR, CD3, CD4, CD8, CD34, PD1 and more. As described in our previous publications, side-by-side comparison of the binding efficiency of MBs and magnetic beads has shown that both formed rosettes with targeted cells with comparable efficiency. However, MBs showed faster binding, with over 85% of cells attached to MBs after 1 min of mixing.

BUBLES is an innovative cell isolation/sorting platform that can be used alone or in combination with the other two major platforms, FACS and MACS, for challenging tasks. This summary mainly focuses on the description and discussion of using BUBLES in the clinical application of cell therapy for the bulk isolation, multiple-marker sorting, and manipulation of human cells in a single container device. However, in other clinical or research situations, BUBLES can also be used alone or in conjunction with FACS or MACS to achieve most optimal results.

FACS (fluoresce activated cell sorting) is the product most used for the detailed analysis of individual cells, and has not been used to scale up for bulk isolation of cells. Magnetic cell sorting (MACS) techniques, particularly the Miltenyi system, are used for targeted cell isolation in bulk. Cells bound to microbeads (e.g. Dynabeads) can be pulled out by an external magnet outside the mixing tube. One of the biggest problems with MACS is that isolated cells coupled to magnetic microparticles (>1 µm) are often destroyed. Therefore, most magnetic cell sorting systems on the market use nanobead over microbead-conjugated antibodies. Existing MACS technology applies high-gradient magnetic cell separation columns to magnetize nanobead-labeled cells in a magnetic field, generated by a strong external magnet. MACS uses ferromagnetic steel-wool filled columns to strengthen the long-distance interaction between the low magnetic nanobeads and the external magnet. However, the use of the steel-wool packed column in this system creates other technical problems such as column clogging and increased manufacturing costs. Moreover, MACS nanobeads stick to the targeted cells, either on the cell surface or inside by endocytosis. This limits the application of MACS primarily to cell enrichment based on a single surface marker.

Figure 12:
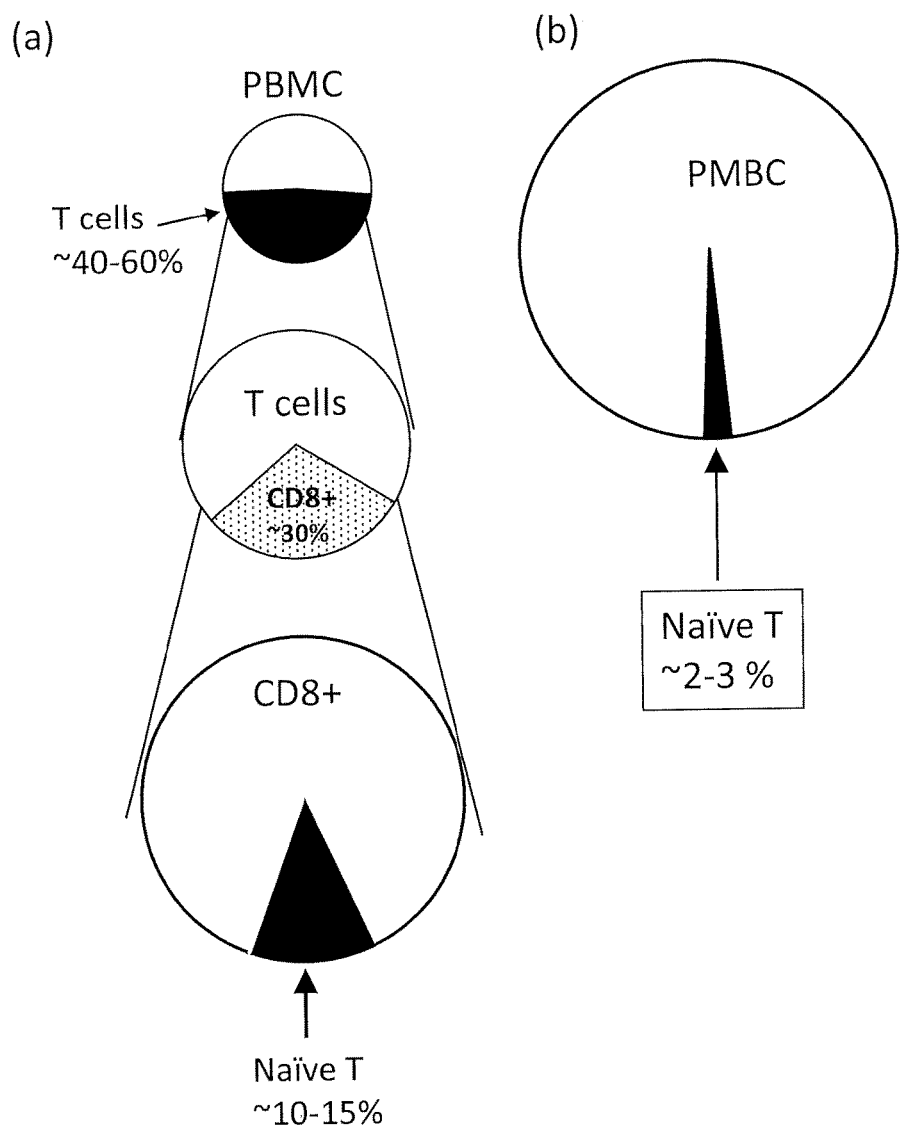
FIG. 12 describes an example of naïve T cells that are a rare population in blood.
Figure 13:
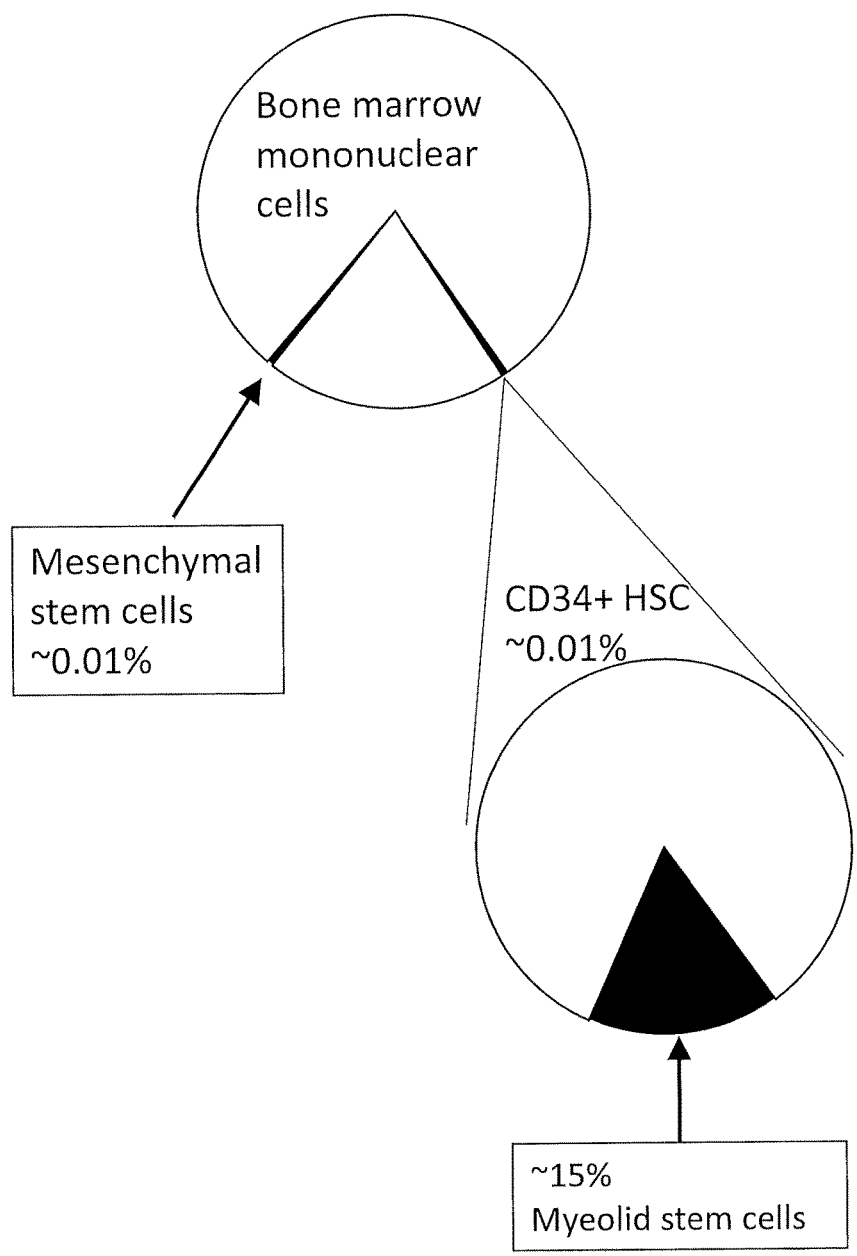
FIG. 13 describes an example of stem cells that are a rare population in tissues, here bone marrow.
Figure 14:
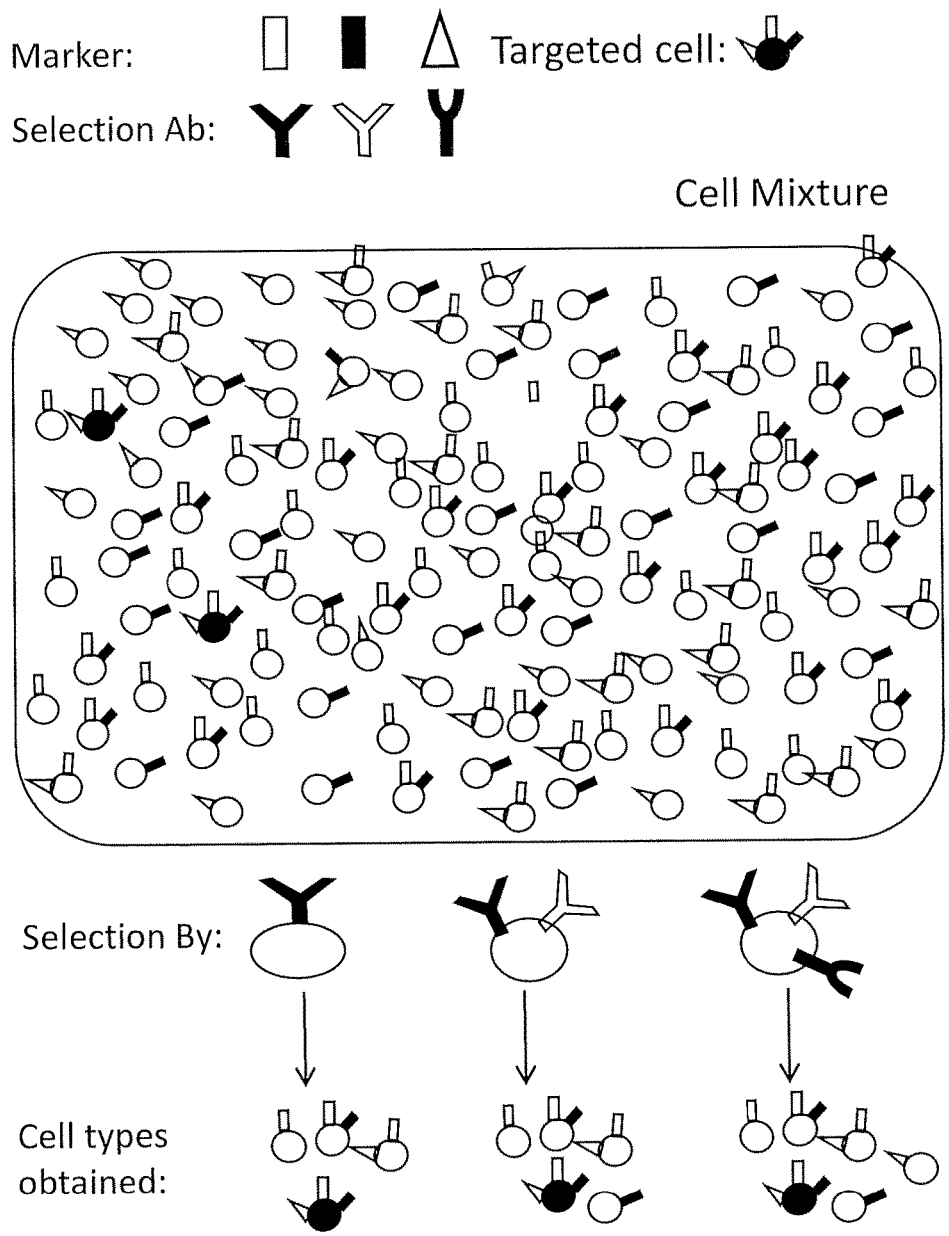
FIG. 14 demonstrates a first prior art selection strategy that results in a low targeted cells concentration mixed with other undesired cell mixtures.
Figure 15:
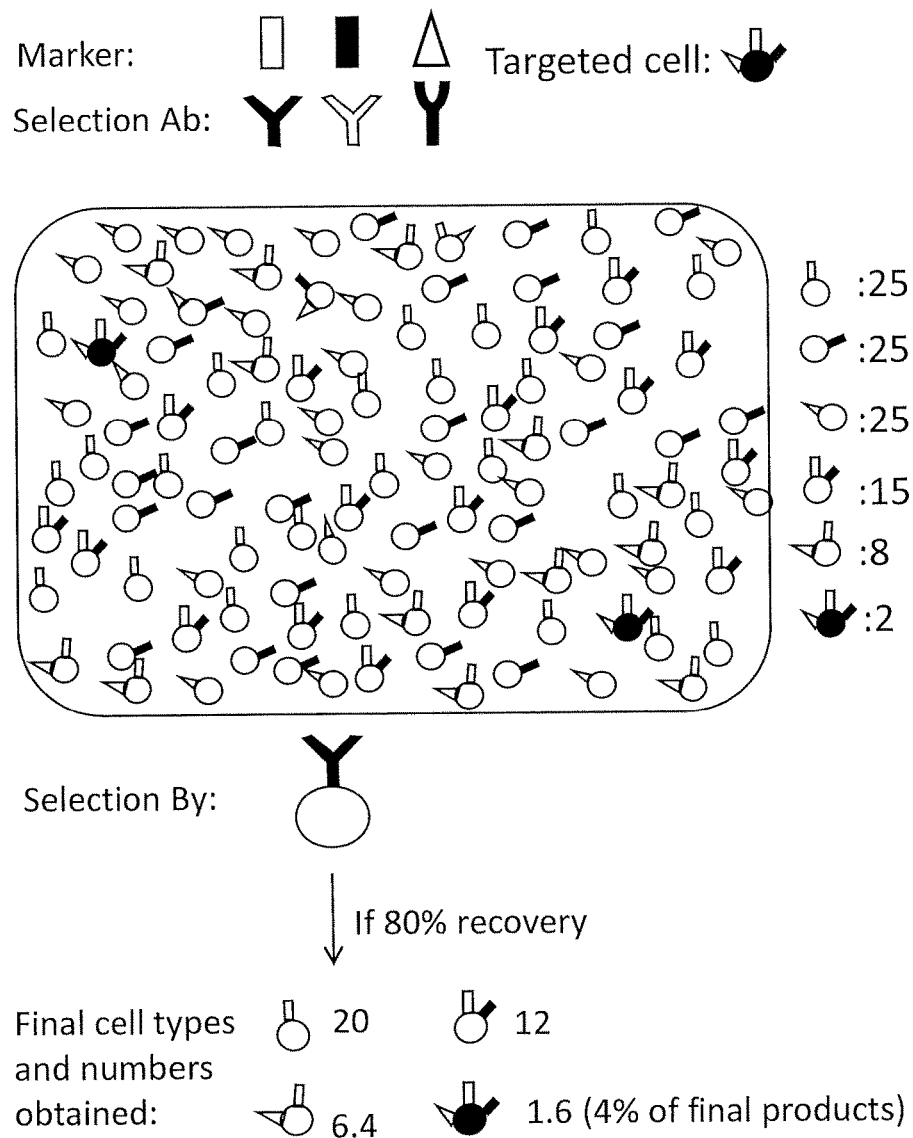
FIG. 15 demonstrates a second prior art selection strategy that results in a low targeted cells concentration mixed with other undesired cell mixtures.
Figure 16:
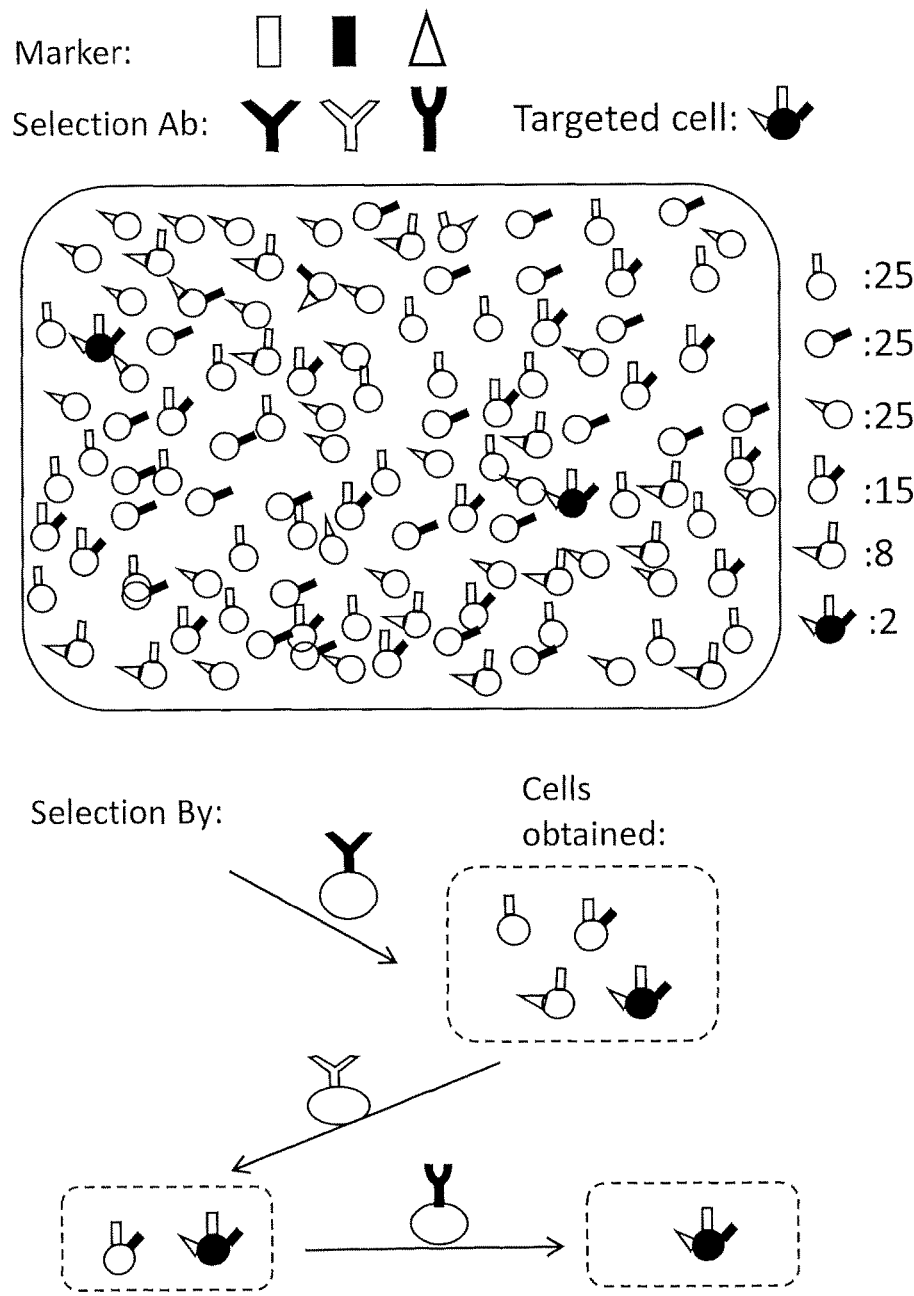
FIG. 16 demonstrates a selection strategy that results in a high targeted cells concentration that may only to a comparatively minor extent mixed with other undesired cell mixtures.

BUBLES Technology Provides the Serial Positive or Negative Selection to Isolate Rare Targeted Cells from Heterogeneous Cell Mixtures The majority of cell therapies in clinical trials today are stem cells or immune T cells that are rare population in blood or tissues, examples are described in FIGS. 12 and 13. Despite overwhelming preclinical data indicating the benefit of tumor-redirecting less-differentiated T-cell subsets, clinical trials have largely used CAR-engineered T cells derived from peripheral blood mononuclear cells (PBMCs) by MACS using a single selection. As described in FIGS. 14 and 15, this selection strategy generates inconsistent cell products consisting of low targeted cells mixed with other undesired cell mixtures. An insufficient therapeutic dose of targeted cell infusion is highly likely to lead to sub-optimal clinical benefits in patients. Serial selection is able to generate high purity and enrich the quantity of targeted cells as described in FIG. 16. A strategy enabling the reversible binding of cells and affinity ligand-conjugated magnetic beads has been recently described. For example, the Streptamer technology enables the reversible target cell binding of magnetic microparticles or nanoparticles by conjugating to Strep-Tactin multimerized low-affinity single-chain antibodies that have been engineered to fuse with a Strep-tag. Other technologies use modified antibodies that can dissociate from cells or magnetic beads. These methods usually require extensive modifications to the antibodies of interest and greatly increase the manipulation steps and complexity. In contrast, BUBLES technology uses a method which can conjugate any desired antibody that is well established, or readily commercial available, or any particular antibody based on the special research and clinical needs. Microbubbles can be disrupted by application of higher ambient pressure (such pressure is well tolerant by mammalian cells) within the device, this advantage of BUBLES technology enables a serial positive or negative selection of multiple cell surface markers to isolate and purify the targeted cells from cell mixtures. Furthermore, this method without negative physical impact on cells results in additional benefits to preserve cell activity and characteristics, which will be discussed further in the later section.

Figure 17:
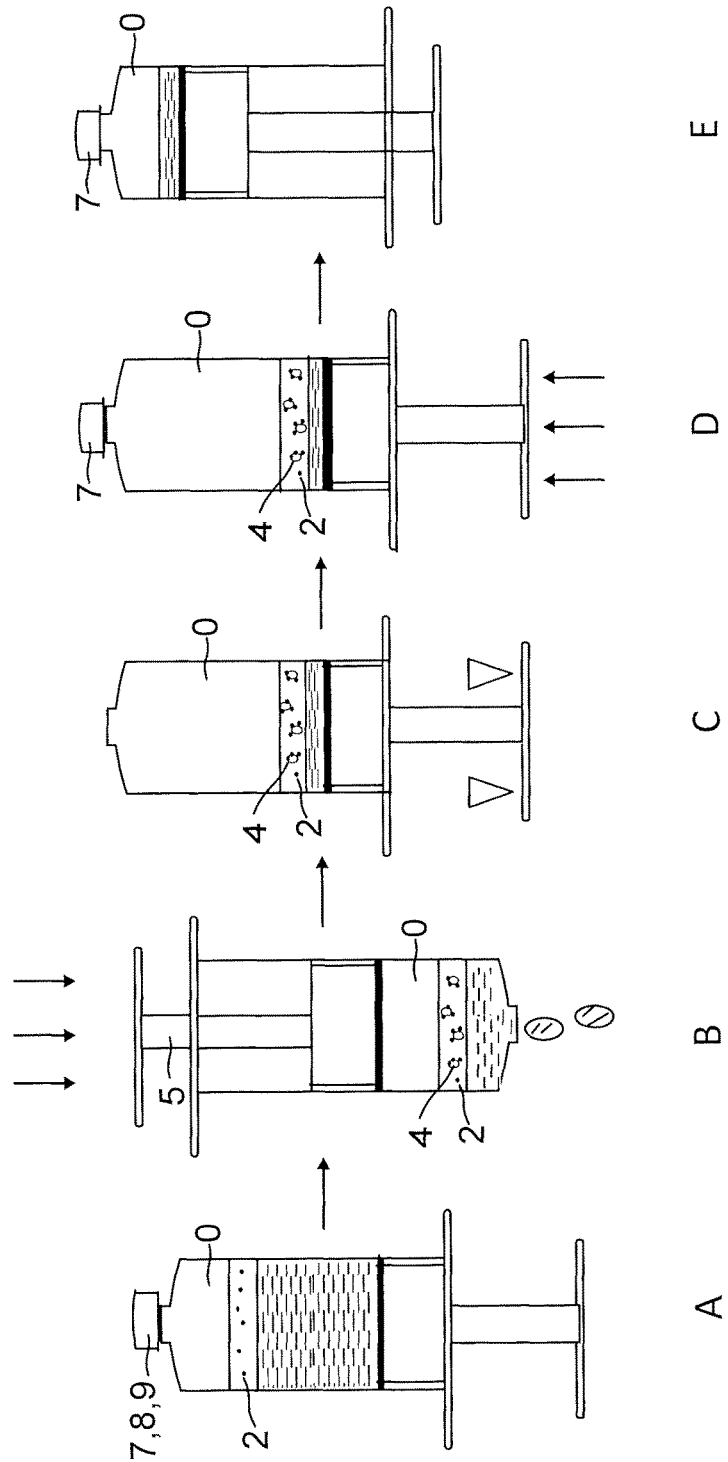
FIG. 17 demonstrates production steps in cell therapy by positive serial selection.

BUBLES Technology Enables Selection, Sorting, Culture, Gene Transduction, and Many Other In Vitro Manipulations in a Single Container One of the most important concepts of GMP manufacturing cellular therapies is to maintain the cells in a system that is closed to the external environment to maintain the sterility of the products throughout the collection and manufacturing process. The distinct four advantages of BUBLES allow multiple in vitro manipulations in one single container in an easy operating and cost-effective fashion for cell therapy production. Here the CAR-T-CD19 cell therapy is used as an example to describe the production steps as described in FIG. 17. In FIG. 17, a first configuration denoted A is shown, where a starting material apheresis PBMC ($\sim 10^9$ cells in 8-9 ml) obtained from blood bank or clinical center is transferred to a BUBLES syringe-like container 3. Microbubbles 2 targeting a first cell surface marker of the targeted cells that are a sparse subset of the cell mixture in the PBMC as a sample are added. About a third of the inner volume airspace within the syringe-like container 3 is left as airspace 0. In this configuration A, the mixture of PBMC and microbubbles 2 is allowed to incubate for example for 10-60 minutes. Optionally, a buffer or media may be added for dilution. In this configuration A, the top of the device is closed by a cap 7 or a Luer Lok 8/adaptor 9 combination as for instance shown in FIG. 5 after the PBMC sample, the first set of microbubbles 2 and optionally the diluent and/or media were place inside the container 3. As shown in configuration B, the container 3 is then inverted and the waste 12 discarded by pushing down the plunger 5. As shown in configuration according to FIG. 3, the waste 12 that includes the non-targeted cells that did not bind to the microbubbles 2 has been discarded since the distance by which the plunger 5 is pushed determines how much of the content within the container 3 is discarded, the plunger is only pushed so far that the microbubbles 2 with the cells bound to the microbubbles 2 remain within the container 3. If useful, cell washing steps could be applied before moving to the next steps in the cell selection process. The next step is demonstrated by configuration C, namely the syringe—like container 3 is turned around again and the plunger 5 is pulled out, increasing the AL volume within the container 3. As a next step, the cap 7 or the Luer Lok 8/adaptor 9 combination is installed again, sealing the container 3, so that in the next step depicted by configuration D the air pressure is increased within the container by pushing up the plunger 5, decreasing the air volume within the container 3. This results in disruption of the microbubbles 2, and detaches the cell mixture selected so far from the microbubbles 2 as depicted by configuration E. After optionally adding again a diluent or media, the steps depicted by system configurations A-E in FIG. 17 can be repeated for a second set of microbubbles targeting a second cell surface marker of the targeted cells.

Materials including microbubble conjugated antibodies, buffer or culture media, cytokines, etc. can be added or discarded through Luer Lok mechanism to maintain sterility of a closed system as illustrated in FIG. 17. Especially, microbubble behaving as a self-floating vehicle and with the self-concentrating/aggregating property, BUBLES system can separate and concentrate desired fractions within the same container by simply inverting the container, in addition, applying ambient pressure to disrupt bubble can easily break the antibody conjugation to make the serial selections possible in one container. In addition, the entire manipulation can be easily configured to automation mode to streamline the GMP manufactures.

Since the selection process through a plurality of subsequence election steps takes place within one and the same container without moving the targeted cells, the method and system according to the invention also provide the advantage of maintaining a sterile environment throughout the process. This advantage can be further extended to also provide for cell activation and cell expansion within the same sterile environment, namely within the container holding the sparse subset of cells at a high concentration after the multiple subsequence election processes have been completed. For this purpose, the cap 7 or Luer Lok 8/adaptor 9 combination can be replaced by an air filter, and for example for CAR-T cell therapy, a CAR gene transduction can be performed within the container 3 by adding retroviral vectors to the isolated cells. Further, optionally microbubbles binding to CD 19 cell surface markers CD 19 expressed T-cells. In the alternative, or in addition, the selected cells may be transferred to a culture bag for scaling up cells, but these steps could also, in the alternative, be performed within the container 3. Additional microbubbles for concentration may then be added to the container, and the buffer may be exchanged for making the isolated and expanded/activated cells with the exchanged buffer suitable for administration to the patient. Even if it is chosen not to perform all steps within one and the same container 3, at least a major part of these steps may be performed with in that container and therefore significantly lower the risk of contamination throughout the selection+ expansion/activation process.

In contrast, other methods and platforms (such as MACS or Streptamers) require changing bags or containers in each step, and require wash and centrifugation to change buffer or concentrate cells. For comparison, A prior art process includes incubating an apheresis product with anti-CD3/anti-CD28 paramagnetic Dynabeads at a ratio of 3 CD3+ cells to 1 Dynabeads, and isolating the CD3+ cell fraction by exposure to a magnet. After washing and re-suspending the selected cells in an initiation medium with low IL-2 concentration and two days of culture, the cells and beads were added to culture bags that had been treated with RetroNectin and loaded with anti-CD 19 CAR new culture bags and viral vector and incubated for at least 24 hours. This transduction step was repeated the day after, and the cells and beads were then transferred to new culture bags and expanded for nine more days. At the completion of the cell expansion, the beads were removed and discarded by again applying the magnet, and the cells were washed and prepared for infusion.

FIG. 23 shows a chart summarizing a comparison between the three methods MACS, Streptamers and Microbubbles.

Every extra step of operations will influence the yield of cell products and directly add stress on cell health and activity. Besides a few steps that can be operated by automation, a huge amount of labor is required to ensure proper performance of those complicated and multiple steps. Furthermore, the culture bags and sterile tubings are costly as the current MACS system demands a great amount of these GMP materials. Steptamers system also needs similar demand of multiple complicated procedures in addition to the extensive and unpredictable antibody engineering work.

Because of the 4 distinct properties of the microbubble, the described BUBLES system provides a variety of advantages over current available system used in clinic, including:

(1) select, isolate, purify, and enrich the rare targeted cell subsets from blood or human tissues using serial positive or negative selections of surface markers, (2) no extra work to engineer Ab, use any readily antibody, readily extending the use of this system to many types of cell therapies, (3) all the manipulations can be performed in one single container, to simplify and control manufacture procedures in a closed system, (4) easily to be configured to automation mode, (5) cost-effective by saving from GMP grade tubings and materials. Although the CAR-T cell therapy is used as an example here to describe the system, this system can be of great use for other cell therapies, such as various hematopoietic stem cells, mesenchymal stem cells, neural stem cells, immune T cells, or immune dendritic cells, since microbubble can be easily conjugated with various antibodies to serial select a particular and rare subset of cells to meet the clinical demand. Gene engineering is required in CAR-T cell therapy, and can be performed in a single container of this system. For other cell therapy applications, if a huge amount of cells are needed, BUBLES system also can be flexible to adapt by incorporating culture bag in the procedure flow.

Preserving Cell Characteristics During In-Vitro/Ex-Vivo Manipulations

The classical definition of a stem cell is that it possesses the self-renewal and pluripotent properties. The somatic stem cells are rare cell subsets with the ability to go through cell division while remaining in the undifferentiated state, and are pluripotent to develop to a variety of mature cell types depending on the differentiation signals received. The ultimate success of cell therapy consequently depends on the degrees of stem cell characteristic maintenances (sternness) of the infusion cells. BUBLES not only minimize the physical damages on targeted cells during the in-vitro/ex-vivo operation procedures, more importantly, BUBLES also provides a distinct advantage to preserve and stimulate cell potency through the mechanism of biological significance. CAR-T cell therapy is used as an example here to specifically discuss this issue, it should be noted that similar principles apply to the other stem cell therapies, including HSC, MSC, neural stem cells, and others, for it is important to preserve the stem cell activity of infused cells to achieve the regeneration function in patients.

One-Container Operation Minimizes the Mechanical Damages on Cells

First, BUBLES system minimizes in vitro manipulation steps as discussed previously including: isolation and enrichment of targeted cells, cell culture and expansion, gene transduction, and other manipulations in a single container, plus, no need to wash, centrifuge, resuspend cells between steps. In addition, the most compressible/flexible lipid coated microbubble is self-molding to external forces (e.g. ultrasound and bound cells), in conjunction with gas core, it is a very gentle material for cells. A simple analogy would be eggs (cells) cushioned by air balloons (microbubbles). These favorable advantages of the BUBLES system provide the operational and physical benefits to greatly minimize the cell damages.

Less Differentiated T Cell is the Desired Cell Subset for CAR-T Cell Therapy

T memory stem ($T_{SCM}$) cells are a rare subset of memory lymphocytes endowed with the stem cell-like ability to self-renew and the multipotent capacity to reconstitute the entire spectrum of memory and effector T cell subsets. T cells undergo a sequential loss of proliferative capacity, but acquisition of effector function occurs during the process of differentiation from antigen-inexperienced naïve cells ($T_N$) to CD62L+ central memory ($T_{CM}$), CD62L-effector memory ($T_{EM}$), and effector ($T_E$) T cell subsets. A table demonstrating the hierarchical model of human T cell differentiation is provided as the following table 3 from Gattinoni L, Nat Rev Cancer, 2012; 12(10):671-684:

| | $T_N \rightarrow$ | $T_{SCM} \rightarrow$ | $T_{CM} \rightarrow$ | $T_{EM} \rightarrow$ | $T_{TE}$ |
|---|---|---|---|---|---|
| CD45RA | + | + | − | − | + |
| CD45RO | − | − | + | + | − |
| CCR7 | + | + | + | − | − |
| CD62L | + | + | + | − | − |
| CD28 | + | + | + | +/− | − |
| CD27 | + | + | + | +/− | − |
| IL-Rex | + | + | + | +/− | − |
| CXCR3 | − | + | + | − | − |
| CD95 | − | + | + | + | + |
| CD11a | − | + | + | + | + |
| IL-2Rβ | − | + | + | + | + |
| CD58 | − | + | + | + | + |
| CD57 | − | − | − | +/− | + |

In the hierarchical model of human T cell differentiation, after antigen priming, naïve T ($T_N$) cells progressively differentiate into diverse memory T cell subpopulations, and ultimately, into terminally differentiated effector T ($T_{TE}$) cells. T cell subsets are distinguished by the combinatorial expression of the indicated surface markers. As $T_N$ cells differentiate progressively into the $T_{TE}$ cell type, they lose or acquire specific functional; and metabolic attributes. The nomenclature used in the table above stand for $T_{SCM}$ cell, T memory stem cell; $T_{CM}$ cell, central memory T cell; $T_{EM}$ cell, effector memory T cell.

This suggests that selection of $T_N$ and $T_{CM}$ may provide greater therapeutic potency. A number of preclinical studies have confirmed that naïve T cell is an ideal cell population to employ CAR-T immunotherapy, however, clinical trials have largely employed unselected peripheral blood mononuclear cell (PBMC)-derived T cell populations due to technical difficulty for isolating the relative paucity of naïve T cells in the circulation, and the lack of robust, clinical-grade manufacturing protocols that are capable of generating and maintaining this cell type in vitro. The isolation of less differentiated T cell populations also has the advantage of reproducibly generating more defined T cell products, unselected populations containing high proportions of $T_{EM}$ and effector cells might fail to generate viable clinical products owing to poor in vitro cell expansion. BUBLES system provides a robust manufacturing procedure to generate naïve T cells which can then be driven to differentiate to desired $T_{SCM}$ cells by addition of a panel of cytokines.

Microbubble Recapitulates the Interaction of APC and T Cell in the Immunological Synapse In vitro cell culture of T cells is essential for receptor engineering and cell expansion to achieve sufficient dose for immunotherapy. However, naïve and less differentiated T cells undergo a rapid loss and maturity development during cell culture and expansion period, and present distinct outcomes of each T cell subset by different differentiation protocols. Besides culture media and serum, various cytokines and Ab/stimulators are necessary to be included in the culture. Typically, the addition of IL-2 is required to promote T cell proliferation, but to also induce some degree of T cell maturation, IL-7, IL-15, and IL-21 are supplemented to maintain memory T cell phenotype. It is important to maintain T cell receptor activity during the in vitro culture to ensure the function and activity of the targeted T cells by stimulation of T cell receptor (TCR), anti-CD3 (or plus anti-CD28) need to be presented on the surface of either artificial synthetic material (e.g. magnetic microparticles) or feeder cells (e.g. PBMC or K562 cells) to mimic the immunological synapse formation between the T cells and antigen presenting cells (APCs) as illustrated in FIG. 18. Artificial APCs (aAPC) derived from non-professional cells (feeder cells) or solid microparticles have been reported with varying degrees of success. It is preferable to use synthetic aAPC for developing in vitro assays and large scale production, to have a better controlled system for robust scale up manufacturing protocol. Indeed, it has been reported that the expression of HLA on living cells fluctuates over time. On the other hand, solid particle based aAPC suffers from another issue of ligand immobility, which would interfere with the dynamic process of immunological synapse formation. Studies had also shown that addition of Dynabeads-CD3/CD28 into the in vitro T cell expansion caused rapid loss of naïve and memory T cells.

Immunological Synapse

Physical T cell-APC contact sets up an axis for polarization of TCR, adhesion molecules, kinases, cytoskeletal elements, and organelles inherent in this mode of juxtacrine signaling. Further lateral organization of the TCR and adhesion molecules into radially symmetric compartments, the immunological synapse, revealed an intersecting plane of symmetry and potential for regulated symmetry breaking to control duration of T cell-APC interactions. In addition to organizing signaling machinery, the immunological synapse directs the polarized transport and secretion of cytokines and cytolytic agents across the synaptic cleft and is a site for the generation and exocytic release of bioactive microvesicles that can functionally affect recipient APC and other cells in the environment, see FIGS. 18 and 19.

As shown in FIG. 18, T cell-mediated immune response begins with the display of a peptide, derived from a pathogen or other biological structure and loaded in a major histocompatibility complex (MHC, creating a pMHC), on the surface of an APC. This pMHC complex is recognized by a T cell receptor (TCR) complex to initiate a cascade of intracellular signaling. Many additional receptor-ligand complexes between T cell and APC in this small (~75 $\mu m^2$) region of immunological synapse (IS) have been observed and can be varied dependent on many factors, including the type of T cell and APC that are participating in this interaction and the presence of soluble factors in the environment. However, two key signaling systems in addition to TCR-pMHC are the major focus. The first of these is CD28, a member of the immunoglobulin superfamily of proteins that is presented on the T cell surface. Upon ligation with either CD80 or CD86, CD28 provides a costimulatory signal that augments TCR-based signaling and is essential for full activation of naïve T cells. The second system is LFA-1, a member of the integrin family of receptors, which binds to ICAM-1 on the APC and provides cell-cell adhesion as well as a costimulatory function. Concurrent engagement of TCR with LFA-1 and/or CD28 provides activation of many types of T cells, and these three receptors form a core set of signals that is well suited for in vitro, reductionist studies of T cell function.

Figure 19:
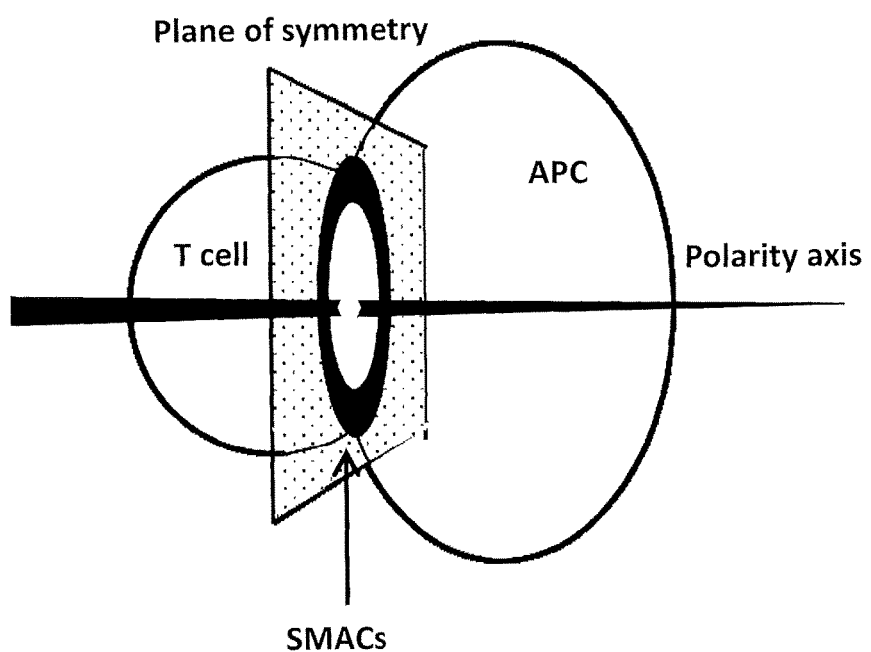
FIG. 19 schematically demonstrates that receptor-ligand pairings in the immunological synapse are organized in distinctive patterns including polarity and symmetry.

As shown in FIG. 19, a striking feature of the IS is that receptor-ligand pairings within this interface are organized into distinctive patterns of micrometer scale and smaller consisting of a micrometer-scale central Supramolecular Activation Cluster (cSMAC) region surrounded by a peripheral Supramolecular Activation Cluster (pSMAC) corresponding to zones of concentrated TCR-pMHC and LFA-1ICAM-1 binding, respectively. Specifically, FIG. 19 demonstrates polarity and symmetry in the mature immunological synapse. Most importantly, the dynamic and molecular components of the interaction complex between TCR and APC within the immunological synapse determine the subsequent proliferative and lineage fate of the T cells. Different T cell-APC interactions produce distinct outcomes, suggesting that the microscale and nanoscale organization of the IS conveys part of the language of communication between T cells and APCs. Importantly, these structures are observed in the 'mature' IS and highly dynamic IS over the initial few minutes of interaction. Understanding the full impact that IS structure and dynamics have on T cell function, as well as the underlying mechanisms, remains a contemporary challenge in immune cell biology due to the lack of a useful experimental tool that is able to better recapitulate the dynamic complexity of IS structure.

Another fundamental issue is that signaling downstream of TCR, CD28, and LFA-1 is associated predominantly with phosphorylation cascades, involving intermediates that are soluble in the cell cytosol. Such molecules typically exhibit mobility that is high (diffusion coefficients on the order of $\mu m^2$/millisecond) relative to the rates at which protein activity can be regulated; it is difficult to obtain graded concentrations of activity of these molecules over the micrometer-scale distances that define the IS. In addition, TCR/CD28/LFA-1 signaling also involves intermediates that are associated with the cell membrane, either stably via a transmembrane domain or transiently through post-translational attachment of lipids or binding to specific membrane components, and thus typically exhibit diffusion coefficients on the order of $\mu m^2$/second, values that make spatially resolved cell signaling at these scales plausible. TCR signaling also involves activation of pathways that modulate the assembly, disassembly, and activity of the cytoskeleton, allowing for spatial regulation of signaling at scale of micrometers and smaller.

Artificial Surfaces for Cell Contact Dependent Interaction

Artificial or engineered surfaces capturing specific aspects of the extracellular environment play a central role in research of cell-cell contact (juxtacrine) signaling. As the above background introduction briefly summarized, although CD3 and CD28 antibodies can be used as the core TCR complex to mimic the ligand-receptor interaction, the artificial system also needs at least to recapitulate (1) dynamic complexity of archetypal IS structure, (2) the mobility and spatial interaction of molecules on cell membrane to better trigger intracellular downstream signaling, and (3) the underlying cytoskeletal network that interacts with membrane proteins in numerous ways and over multiple distance scales ranging from micrometers to tens of nanometers.

For example, elastomers and hydrogels of controlled elasticity have been used very successfully in the context of understanding how stromal cells sense the rigidity of the ECM, however, such engineered systems have been proven difficult to capture the interaction between T cells and APCs which exhibit additional mechanical response and cellular properties. The use of a micropatterned surface and multicomponent micropatterned surfaces presenting patterns of ligands to TCR complex within the IS is the next advance to understand cell signaling, However, a fundamental limitation is that such systems do not capture the natural mobility of the proteins along the APCs surface. FIG. 19 demonstrates the polarity and symmetry in the mature immunological synapse. Supramolecular activation clusters (SMACs) are shown in the interface between T cell and APC. The axis of directed secretions is the spear passing through the SMAC. The plane of symmetry is the plane of the immunological synapse, which is radially symmetric when stable. The T cell will migrate if the adhesion ring breaks symmetry. The fact of the immobilization influences signaling events has made this technology limited in use in research understanding of cell signaling and communication, and not suitable for large scale of T cell activation. The third example is a self-assembled planar bilayer structure of phospholipids. A combination of hydration, van der Waals, and other forces maintains the bilayer in close proximity to an appropriate substrate, most commonly glass. A thin (sub-nanometer) layer of water separates the bilayer and support, imparting lateral mobility of the phospholipids and other membrane components, including tethered proteins, in the plane of the bilayer.

Surface-immobilized and membrane-tethered ligands to receptors on the T cell surface thus represent two experimental extremes, with the real APC membrane being somewhere between these states, owing to the microscale and nanoscale details of cellular structure. In the fourth method, a silicon oxide surface, which is one of only a handful of materials that support bilayer formation, is patterned with nanoscale barriers of another material that does not support bilayer formation, such as metal or plastic. This model is too complicated to be used in industrial scale.

The above described examples are used in research understanding and will not be practical to be converted for industrial use due to the extreme low through put scale and the material complexity of forming such systems. The current standard protocol for T cell activation is the addition of Dynabeads conjugated with CD3 or plus CD28 antibody which act as an artificial activator, as described above. Microscale magnetic beads are designed to have similar cell size to mimic an APC, conjugation of CD3 and CD28 is to trigger the ligand-TCR binding to simulate stimulation signal via TCR complex. However, studies have shown that the addition of Dynabeads-CD3/CD28 into the in vitro T cell expansion has caused rapid loss of naïve and memory T cells. A simple analogy would be eggs (cells) sandwiched with rocks (microparticles). Therefore, the majority of current magnetic cell sorting systems on the market use nanobeads, which is analogous to eggs (cells) surrounded by sand (nanoparticles) for cell isolation. However, these ligands conjugated nanoparticles are insufficient to activate T cells, perhaps not only because of the rigid nature of nanobeads, but also because the small size of the particles is not able to induce formation of immunological synapse. With the understanding of the complexity of immunological synapse, the problem of Dynabeads to recapitulate the biological function of APC could be due to failing to trigger appropriate signal transduction pathway in T cells because of both rigid and precipitation property of magnetic beads. Potentially, the mobile lipid surface of MBs may provide the necessary dynamic IS structure upon ligand-TCR engagement.

Experimental Demonstration

Figure 21:
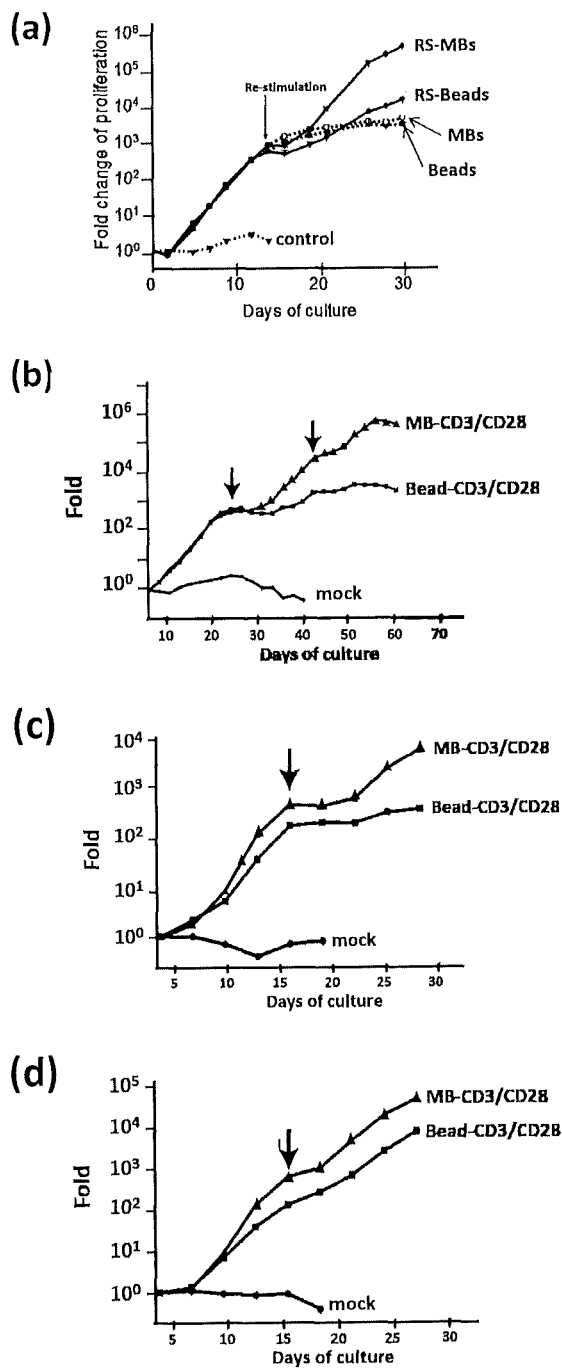
FIG. 21 demonstrates comparison of T cell expansion by using anti-CD3/CD28 conjugated Dynabeads and anti-CD3/CD28 conjugated microbubbles for one or more re-stimulations with different blood donors.

The effects on T cell activation were tested using Dynabeads vs. microbubbles. Microbubbles conjugated with anti-CD3/CD28 outperformed anti-CD3/CD28 Dynabeads on T cell expansion, especially after the second stimulation. As shown in FIG. 21, T cells from PBMC were robustly expanded after the first stimulation with anti-CD3/CD28 conjugated Dynabeads or microbubbles within the initial 2 weeks. Remarkably, while the microbubbles based T cell expansion continued the same trend with the subsequent two stimulations; the Dynabeads based expansion dramatically decreased after the $2^{nd}$ stimulation (FIG. 21, diagram a). The T cell expansion is dependent on anti-CD3/CD28, as it stopped when no stimulating reagents were added when the $2^{nd}$ stimulation was performed (FIG. 21, mock or control groups). Results are reproducible using PBMCs from the same donor (FIG. 21, diagrams a and b), or different donors (FIG. 21, diagram b, c and d). A study from Li et al. reported similar observations by comparing T cell responses stimulated by anti-CD3/CD28 Dynabeads and soluble anti-CD3 in the presence of Fc receptor bearing feeder cells, which was designated the "Rapid Expansion Protocol" (REP), in which the feeder cells serve as APCs to present anti-CD3 (bound to its Fc receptor) and B7 (CD80 and CD86, equivalent to anti-CD28). Microbubbles and feeder cells are surrounded by fluid lipid surfaces such that the responses of T cell survival, proliferation, and phenotype after stimulation should be similar with REP and microbubbles. On the other hand, feeder cells need to be removed from the culture while removal is not required in MB based T cell activation. Therefore, microbubbles based aAPCs have a number of advantages over Dynabeads and REP as described in the following table 4:

|  | Anti-CD3/CD 28 Microbubbles | Anti-CD3/CD 28 Dynabeads | REP, "Rapid Expansion Protocol" |
| --- | --- | --- | --- |
| Surface | Lipid | Solid beads | Lipid |
| Feeder cells needed? | No | No | Yes |
| Destructible | Yes | No | No |
| Particles/feeder cells removal? | No | Yes | Yes |
| Ligand density adjustable? | Yes | Yes | No |
| Cytokine source | Extrinsic | Extrinsic | Intrinsic, uncontrolled |
| Dynamics in cell junction? | Yes | No | Yes |
| Mobility of interactions? | Yes | No | Yes |

Figure 22:
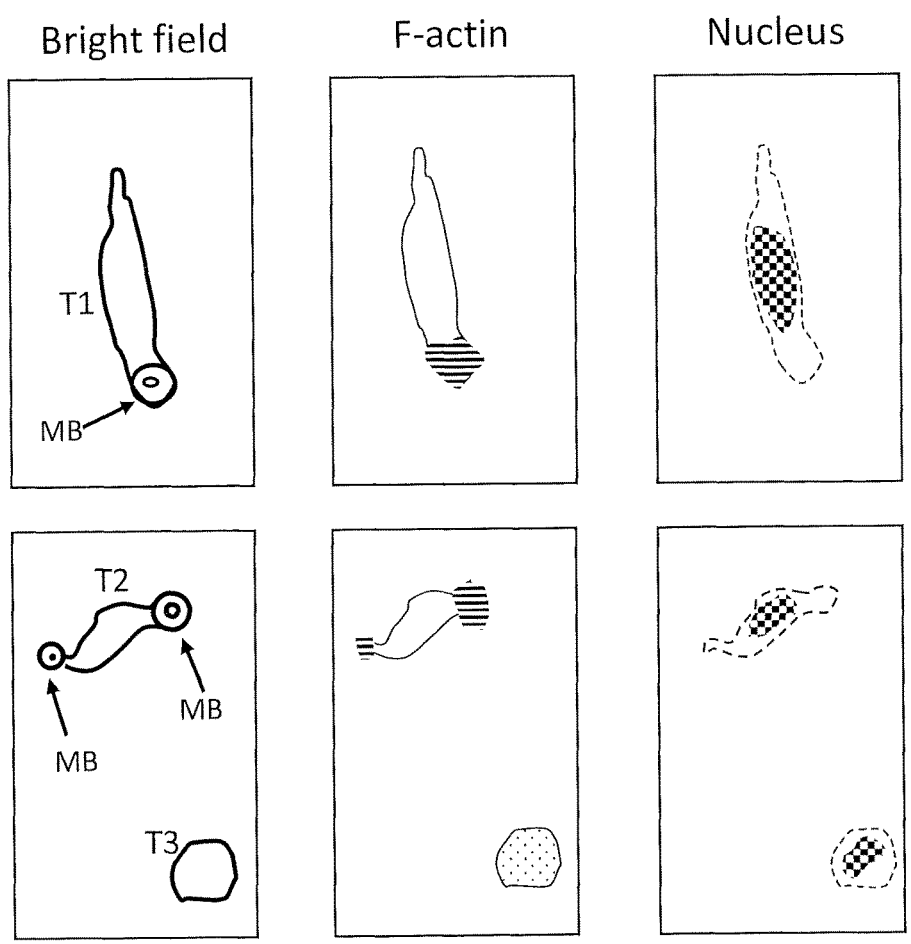
FIG. 22 demonstrates formations of immunological synapse between T cells and anti-CD3/CD28 conjugated microbubbles by fluorescence staining.

FIG. 22 demonstrates the sketch of the immunological synapse formation between T cells (indicated by T1 and T2) and anit-CD3/CD28 conjugated microbubble (MB by arrows) by immune-fluorescence assay. Note the shape of the T cell is polarized with F-actin polymerization band near the contact zone with MB as seen in F-actin staining panels. The T cell that is not associated with MB (T3) has typical even-distributed F-actin staining within the cell. The cell nucleus is stained with DAPI to show the cell integrity.

Furthermore, microbubbles would spontaneously burst within 10-16 hours in standard culture conditions at 37° C. This unique property of microbubbles may provide additional advantages over Dynabeads to avoid over-stimulation of T cells which could leads to exhaustion of T cell activity and better mimic immunological synapse formation duration as it has been shown that IS formation requires only a few hours. Furthermore, this interesting property of microbubbles not only eliminates the need for bead removal, which would reduce the chance of contaminations and the complexity for automation.

Microbubble Based Technology Serves as a Powerful Tool for Other Biological Systems The importance of spatial considerations in IS signaling is also seen in all types of cell-cell and cell-ECM communication. Communication between cells is carried out not only by the signaling molecules themselves, but also by many contextual and positional cues that arise from the way the signal is distributed and presented to the receptor. Transmembrane and secreted growth factors signal to their receptors in contact-dependent association with extracellular matrix (ECM) components and integrins. Signaling molecules can also reach cells at a distance via cytonemes that contact and activate the target cells through synapse-like structures. Besides the above described immunological synapse system, many other cell-cell and cell-matrix contact systems play critical roles to regulate a variety of biological functions. Similarly, selected ligands conjugated microbubbles can serve as artificial cells to recapitulate these interactions.

The above description of the disclosed embodiments is provided to enable any person skilled in the art to make or use the present disclosure. Various modifications to these embodiments will be readily apparent to those skilled in the art, and the generic principles described herein can be applied to other embodiments without departing from the spirit or scope of the present disclosure. Thus, it is to be understood that the description and drawings presented herein represent a presently preferred embodiment of the present disclosure and are therefore representative of the subject matter, which is broadly contemplated by the present disclosure. It is further understood that the scope of the present disclosure fully encompasses other embodiments that may become obvious to those skilled in the art.

Further Embodiments are Given in the Following Paragraphs:

1. A buoyancy enabled separation method for isolation from a sample including a variety of different cells a sparse subset of cells that is differentiated by a plurality of different cell surface markers, comprising: a) placing the sample in a container; b) adding first flexible shell microbubbles having a flexible shell with an inner bubble wall enclosing a gas and an outer bubble wall conjugated to a first antibody capable of binding to a first cell surface marker of a first subset of cells encompassed in the liquid sample; c) incubating over a time span sufficient to allow an interaction between the first antibody and the first cell surface marker binding the first antibody to the first cell surface marker; d) allowing the first microbubbles with the first subset of cells bound to the first microbubbles to separate by flotation from a remainder of the sample; e) removing waste from the container, including cells within the sample other than the first subset of cells; f) disrupting the first microbubbles such that the first set of isolated cells are no longer buoyant; g) adding second flexible shell microbubbles having a flexible shell with an inner bubble wall enclosing a gas and an outer bubble wall conjugated to a second antibody capable of binding to a second cell surface marker of a second subset of cells encompassed within the first subset of cells; h) incubating over a time span sufficient to allow an interaction between the second antibody and the second cell surface marker binding the second antibody to the at least one second cell surface marker; i) allowing the microbubbles with the second subset of cells bound to the microbubbles to separate by flotation from a remainder of the sample; and j) removing waste from the container, including cells within the first subset of cells other than the second subset of cells.

2. The method according to embodiment 1, wherein the first and second cell surface markers is one of CD8, CD62L, CD45RA, CD3 and CD28.

3. The method of embodiment 1, further comprising: k) disrupting the second microbubbles such that the isolated first set of cells are no longer buoyant; and l) repeating steps g) through k) for a third subset of cells by applying additional flexible shell microbubbles conjugated to not previously used antibodies capable of binding to targeted cell surface markers that have not been previously targeted.

4. The method of embodiment 3, wherein the cell surface markers are CD8+, DC62L+ and CD45RA+, and the sparse subset of cells are naïve T cells.

5. The method of embodiment 4, further comprising repeating step l) for the nth subset of cells by applying additional flexible shell microbubbles conjugated to not previously used antibodies capable of binding to targeted cell surface markers that have not been previously targeted.

6. The method of one of embodiments 1-5, further comprising that the method step of removing waste from the container includes removing the waste from the bottom of the container.

7. The method of one of embodiments 1-5, further comprising the method step of removing waste from the container by a negative selection by removing waste in form of undesired cells from the container by binding these undesired cells to respective microbubbles to be buoyant to the top of the container and removing these undesired cells bound to respective microbubbles from that top of the container.

8. The method of embodiment 6 or 7, further comprising that the method step of removing waste from the container includes moving a plunger within the container.

9. The method of any of the preceding embodiments, further comprising that the method step of disrupting the first, second and subsequent microbubbles includes increasing the pressure to which the microbubbles are subjected.

10. The method of embodiment 9, further comprising that increasing the pressure to which the microbubbles are subjected includes moving a plunger within the container.

11. The method of any of the preceding embodiments, wherein the sparse subset of cells includes T-cells and the method further comprises: m) adding to the sparse subset of ligands presenting microbubbles having a flexible shell with an inner bubble wall enclosing a gas and an outer bubble wall conjugated to ligands capable of forming an immunological synapse with the T-cells; o) incubating the T cells with the ligands presenting microbubbles over a time span that is sufficient for activating and expanding the sparse subset of T cells; p) achieving specific T-cell activation through combining with a unique peptide bound to a recombinant MHC, and anti-CD28 or with co-stimulating molecules, such as recombinant CD80 and CD86; and q) achieving nonspecific T-cell activation through combining anti-CD3, and anti-CD28 or with co-stimulating molecules, such as recombinant CD80 and CD86.

12. The method of any of the preceding embodiments, wherein the sample includes a variety of different cells such as one of or a combination of T cells, B cells, tumor-infiltrating lymphocytes, dendritic cells, natural killer cells, endothelial cells, stem cells and cancer cells from human or animal blood, other human or animal body fluids or artificial buffer solutions.

13. The method of any of the preceding embodiments, wherein the isolation of the sparse subset of cells from the sample including a variety of different cells is made by a positive selection, negative selection or a sequential combination of both.

14. A system for performing the method according to any of the preceding embodiments, comprising: a container (3) having an inner wall defining an inner container space; a plunger (5) in sealing connection with the inner wall and a movable in relation to the inner wall; a port with an openable and closeable valve (8, 9) connecting the inner space to the environment for allowing gas, liquid and solid material to be fed into the inner space and out of the inner space; and flexible shell microbubbles (2) within the inner container space, said microbubbles (2) having a flexible shell with an inner bubble wall enclosing a gas and an outer bubble wall conjugated to a first antibody capable of binding to a first cell surface marker of a first subset of cells encompassed in the liquid sample.

15. The system according to embodiment 14, wherein the plunger (5) has a front face that has one of the shapes concave, convex or flat.

16. The system according to embodiment 14, wherein the plunger (5) has an adjustable front face adapted to be changed in shape such as assuming the shapes convex, convex or flat, and the system further comprises an adjustment mechanism for changing the shape of the front face during use of the system.

17. The system according to one of embodiments 14-16, wherein the container (3) is sterile.

18. The system according to one of embodiments 14-17, wherein the container (3) contains a sterile solution that is adapted to keep cells (4) of the samples and biological agent in a viable state.

19. The system according to one of embodiments 14-18, further comprising a mechanical plunging system that is configured to move the plunger (5).

20. The system according to one of embodiments 14-18, wherein the plunging system is automated or computerized.

21. A method for activating and expanding isolated T cells, comprising: a) adding to isolated T cells ligands presenting microbubbles having a flexible lipid shell with an inner bubble wall enclosing a gas and an outer bubble wall conjugated to ligands capable of achieving cell contact dependent juxtacrine signaling on the isolated T cells; b) adding to isolated T cells ligands presenting microbubbles having a flexible lipid shell with an inner bubble wall enclosing a gas and an outer bubble wall conjugated to an antigen capable of forming an immunological synapse with the T cells.

22. The method of embodiment 21, wherein the ligands presenting microbubbles are anti-CD3 and anti-CD28 conjugated microbubbles and the activating and expanding of the isolated T cells is used for preparing the T cells in vitro for adoptive cell transfer, such as in chimeric antigen receptor (CAR-T) cell therapy.

23. The method of embodiment 21, wherein the ligands presenting microbubbles are peptide/MHC and anti-CD28 conjugated microbubbles and the activating and expanding of the isolated T cells is used for preparing the T cells in vitro for adoptive cell transfer.

24. The method according to one of embodiments 21-23, further comprising incubating said cells with the ligands presenting microbubbles over a time span that is sufficient for activating or inhibiting the isolated cells.

What is claimed is:

1. A buoyancy enabled separation method for isolation from a sample including a variety of different cells a sparse subset of cells that is differentiated by a plurality of different cell surface markers, comprising:
   a) placing the sample in a container;
   b) adding first flexible shell microbubbles having a flexible shell with an inner bubble wall enclosing a gas and an outer bubble wall conjugated to a first antibody capable of binding to a first cell surface marker of a first subset of cells encompassed in the sample;
   c) incubating over a time span sufficient to allow an interaction between the first antibody and the first cell surface marker binding the first antibody to the first cell surface marker;
   d) allowing the first flexible shell microbubbles with the first subset of cells bound to the first flexible shell microbubbles to separate by flotation from a remainder of the sample;
   e) removing waste from the container, including cells within the sample other than the first subset of cells;
   f) disrupting the first flexible shell microbubbles such that the first set of isolated cells are no longer buoyant;
   g) adding second flexible shell microbubbles having a flexible shell with an inner bubble wall enclosing a gas and an outer bubble wall conjugated to a second antibody capable of binding to a second cell surface marker of a second subset of cells encompassed within the first subset of cells;
   h) incubating over a time span sufficient to allow an interaction between the second antibody and the second cell surface marker binding the second antibody to the at least one second cell surface marker;
   i) allowing the second flexible shell microbubbles with the second subset of cells bound to the second flexible shell microbubbles to separate by flotation from a remainder of the sample; and
   j) removing waste from the container, including cells within the first subset of cells other than the second subset of cells.

2. The method according to claim 1, wherein the first and second cell surface markers is one of CD8, CD62L, CD45RA, CD3 and CD28.

3. The method of claim 1, further comprising:
   k) disrupting the second flexible shell microbubbles such that the isolated first sot second subset of cells are no longer buoyant; and
   l) repeating steps g) through k) for a third subset of cells by applying additional flexible shell microbubbles conjugated to not previously used antibodies capable of binding to targeted cell surface markers that have not been previously targeted.

4. The method of claim 3, wherein the cell surface markers are CD8+, CD62L+ and CD45RA+, and the sparse subset of cells are naïve T cells.

5. The method of claim 4, further comprising repeating step l) for the nth subset of cells by applying additional flexible shell microbubbles conjugated to not previously used antibodies capable of binding to targeted cell surface markers that have not been previously targeted.

6. The method of one of claim 1, further comprising that the method step of removing waste from the container includes removing the waste from the bottom of the container.

7. The method of claim 6, further comprising that the method step of removing waste from the container includes moving a plunger within the container.

8. The method of one of claim 1, further comprising the method step of removing waste from the container by a negative selection by removing waste in form of undesired cells from the container by binding these undesired cells to respective microbubbles to be buoyant to the top of the container and removing these undesired cells bound to respective microbubbles from that top of the container.

9. The method of claim 8, further comprising that the method step of removing waste from the container includes moving a plunger within the container.

10. The method of claim 1, further comprising that the method step of disrupting the first, second and subsequent flexible shell microbubbles includes increasing the pressure to which the flexible shell microbubbles are subjected.

11. The method of claim 10, further comprising that increasing the pressure to which the microbubbles are subjected includes moving a plunger within the container.

12. The method of claim 1, wherein the sparse subset of cells includes T-cells and the method further comprises:
   m) adding to the sparse subset of cells ligands presenting flexible shell microbubbles having a flexible shell with an inner bubble wall enclosing a gas and an outer bubble wall conjugated to ligands capable of forming an immunological synapse with the T-cells;
   o) incubating the T cells with the ligands presenting flexible shell microbubbles over a time span that is sufficient for activating and expanding the sparse subset of T cells;
   p) achieving specific T-cell activation through combining with a unique peptide bound to a recombinant MHC, and anti-CD28 or with co-stimulating molecules; and
   q) achieving nonspecific T-cell activation through combining anti-CD3, and anti-CD28 or with co-stimulating molecules.

13. The method of claim 12, further comprising r) achieving specific T-cell activation through combining with co-stimulating molecules recombinant CD80 and CD86.

14. The method of claim 12, further comprising r) achieving nonspecific T-cell activation through combining with co-stimulating molecules recombinant CD80 and CD86.

15. The method of claim 1, wherein the sample includes one of or a combination of T cells, B cells, tumor-infiltrating lymphocytes, dendritic cells, natural killer cells, endothelial cells, stem cells and cancer cells from human or animal blood, other human or animal body fluids or artificial buffer solutions.

16. The method of claim 1, wherein the isolation of the sparse subset of cells from the sample including a variety of different cells is made by a positive selection, negative selection or a sequential combination of both.

\* \* \* \* \*